US012594417B2

(12) United States Patent
Forest-Nault et al.

(10) Patent No.: US 12,594,417 B2
(45) Date of Patent: Apr. 7, 2026

(54) SYSTEMS AND METHODS FOR SIMULATING CARDIOVASCULAR FLUID FLOW

(71) Applicants: Catherine Forest-Nault, Montreal (CA); Aymeric Guy, Montreal (CA); Guillaume Febrer, Montreal (CA)

(72) Inventors: Catherine Forest-Nault, Montreal (CA); Aymeric Guy, Montreal (CA); Guillaume Febrer, Montreal (CA)

(73) Assignee: TECHNOLOGIES LIFEENGINE INC., Montreal (CA)

( * ) Notice: Subject to any disclaimer, the term of this patent is extended or adjusted under 35 U.S.C. 154(b) by 249 days.

(21) Appl. No.: 18/569,031

(22) PCT Filed: Jun. 13, 2022

(86) PCT No.: PCT/CA2022/050941
§ 371 (c)(1),
(2) Date: Dec. 11, 2023

(87) PCT Pub. No.: WO2022/256946
PCT Pub. Date: Dec. 15, 2022

(65) Prior Publication Data
US 2024/0278001 A1 Aug. 22, 2024

Related U.S. Application Data

(60) Provisional application No. 63/244,573, filed on Sep. 15, 2021, provisional application No. 63/209,756, filed on Jun. 11, 2021.

(51) Int. Cl.
*A61M 60/851* (2021.01)
*G09B 23/30* (2006.01)

(52) U.S. Cl.
CPC ... *A61M 60/851* (2021.01); *A61M 2205/3334* (2013.01); *A61M 2210/125* (2013.01)

(58) Field of Classification Search
CPC .... A61M 2205/3334; A61M 2210/125; A61M 60/851; G01F 1/72; G01F 25/10
See application file for complete search history.

(56) References Cited

U.S. PATENT DOCUMENTS 10,832,595 B2 11/2020 Richer et al.
2019/0266922 A1* 8/2019 Lemieux .............. G09B 23/303

FOREIGN PATENT DOCUMENTS

EP 3175438 B1 2/2020

OTHER PUBLICATIONS

International Search Report and Written Opinion issued in corresponding International application No. PCT/CA2022/050941 on Aug. 12, 2022.

* cited by examiner

*Primary Examiner* — Jon Eric C Morales
(74) *Attorney, Agent, or Firm* — BCF LLP

(57) ABSTRACT

A system for simulating cardiovascular fluid flow having a target fluid flow profile, which has target pulsatile flow and target systemic resistance components, in a test member is disclosed. The system includes a reservoir, a pump, input and output channels, a first valve in the input channel, a second valve in the output channel, and a processor. The input and output channels are connectable to the test member so as to form a fluid circuit with the test member. The processor is configured to execute a method for controlling the first valve to generate the target pulsatile flow component in the input channel, and controlling the second valve to generate the target systemic pressure component. Other systems are also disclosed. Methods for simulating target fluid flow profiles in a test member are also disclosed.

18 Claims, 18 Drawing Sheets

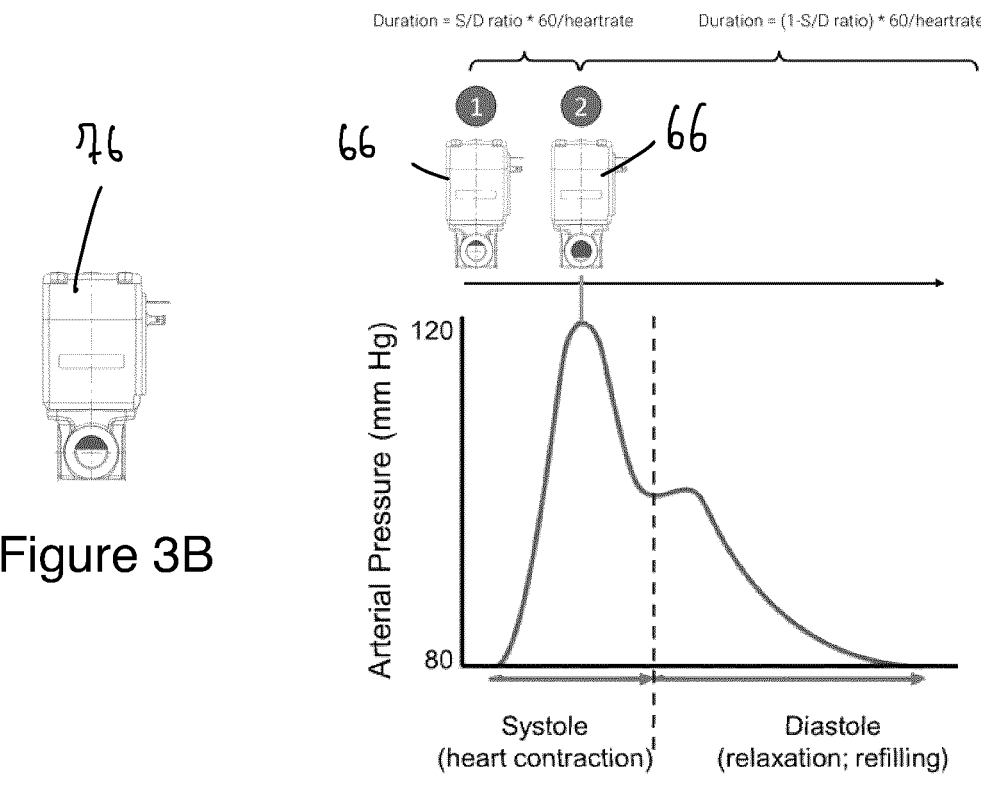
Figure 3B
Figure 3C
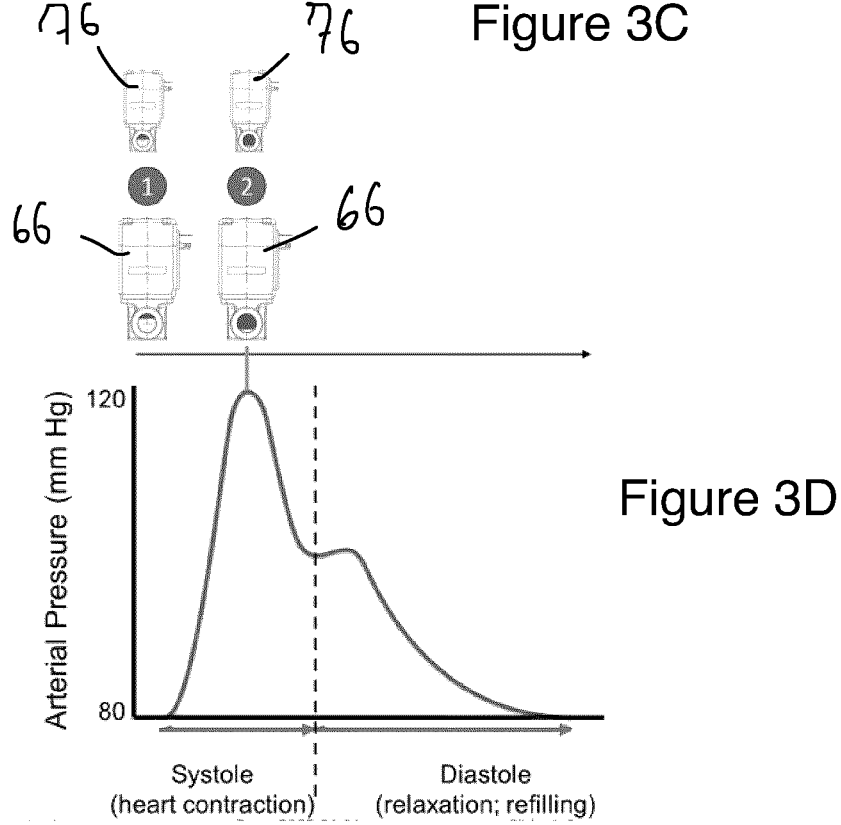
Figure 3D

300

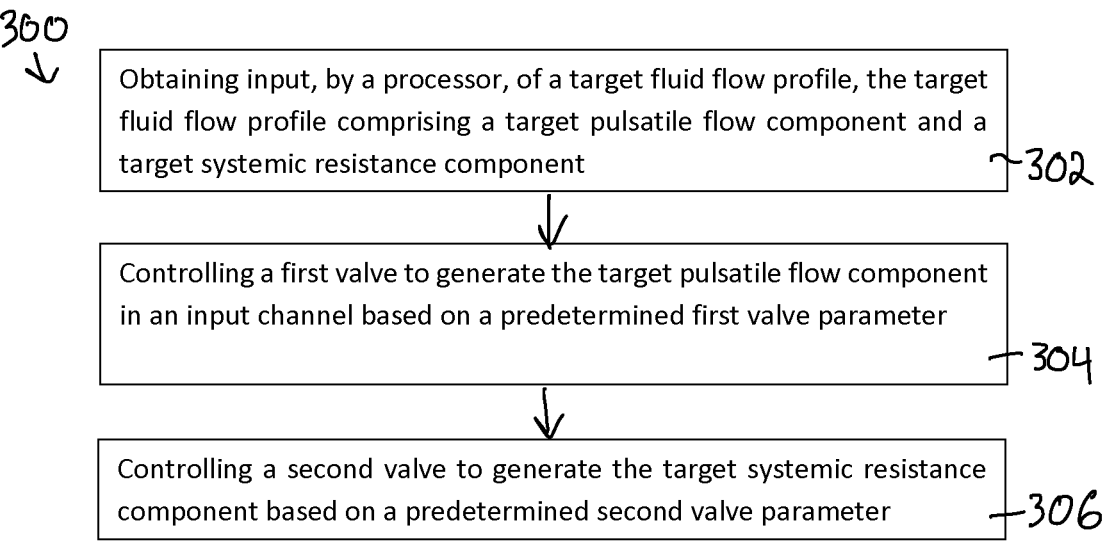

| |
|---|
| Obtaining input, by a processor, of a target fluid flow profile, the target fluid flow profile comprising a target pulsatile flow component and a target systemic resistance component     302 |

| |
|---|
| Controlling a first valve to generate the target pulsatile flow component in an input channel based on a predetermined first valve parameter     304 |

| |
|---|
| Controlling a second valve to generate the target systemic resistance component based on a predetermined second valve parameter     306 |

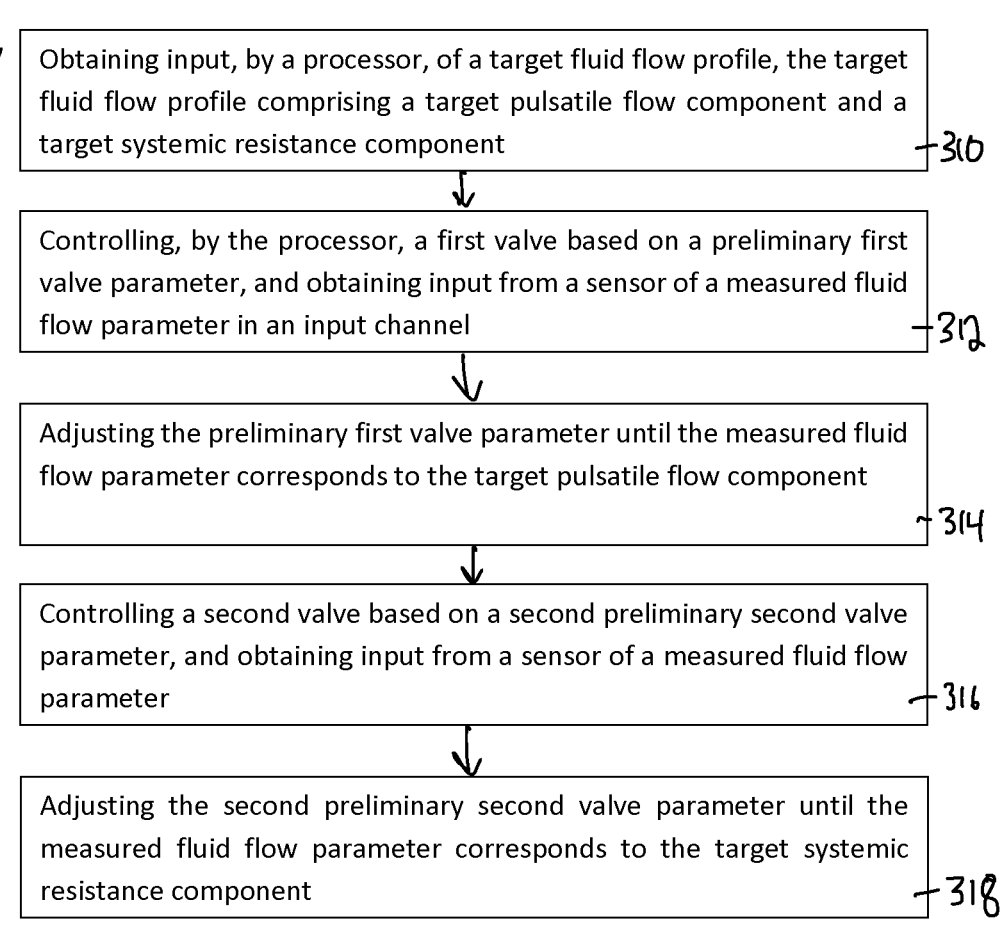

| |
|---|
| Obtaining input, by a processor, of a target fluid flow profile, the target fluid flow profile comprising a target pulsatile flow component and a target systemic resistance component     310 |

| |
|---|
| Controlling, by the processor, a first valve based on a preliminary first valve parameter, and obtaining input from a sensor of a measured fluid flow parameter in an input channel     312 |

| |
|---|
| Adjusting the preliminary first valve parameter until the measured fluid flow parameter corresponds to the target pulsatile flow component     314 |

| |
|---|
| Controlling a second valve based on a second preliminary second valve parameter, and obtaining input from a sensor of a measured fluid flow parameter     316 |

| |
|---|
| Adjusting the second preliminary second valve parameter until the measured fluid flow parameter corresponds to the target systemic resistance component     318 |

Connecting a first artery of a cadaver to an input channel    332

Connecting a first vein of the cadaver to an output channel    334

Connecting a second artery of the cadaver to a second vein of the cadaver to create a fluid path of low resistance inside the cadaver    336

Connecting a first vein of the cadaver to an output channel    338

380

Obtaining input of a predetermined fluid flow profile

382

Causing control elements of perfusion system to independently modulate a first fluid parameter in a first branch of an input channel of the perfusion system and a second fluid parameter in a second branch of the input channel of the perfusion system.

390

SYSTEMS AND METHODS FOR SIMULATING CARDIOVASCULAR FLUID FLOW

CROSS-REFERENCE TO RELATED APPLICATIONS

This application is a national phase filing under 35 U.S.C. § 371 of International Application No. PCT/CA2022/050941 filed on Jun. 13, 2022, which claims benefit of priority of U.S. Provisional Application No. 63/209,756 filed on Jun. 11, 2021, and U.S. Provisional Application No. 63/244,573 filed on Sep. 15, 2021, the contents of each of which are hereby incorporated by reference in their entirety.

TECHNICAL FIELD

The present technology relates to systems and methods configured to simulate cardiovascular fluid flow in a test member, such as but not limited to a cadaver, a portion of a cadaver such as an organ or other cadaver body part, and a synthetic organ or other synthetic body part.

BACKGROUND

Simulation systems are used to simulate cardiovascular flow in non-viable test members such as cadavers, cadavers parts or organs for medical training or for testing of new medical devices or procedures. Such simulation systems are configured to be connectable to a flow path within the cadavers, cadavers parts or organs and to form a fluid flow circuit therewith.

In some examples, such simulation systems are connected to cadavers and the resulting fluid flow circuit is perfused with fluid, and cardiovascular flow generated therein. This can enable the practice of surgical techniques on the cadaver with quasi-realistic feedback of the surgical technique by assessing changes in the cardiovascular flow.

In other examples, simulation systems are connected to synthetic or real organs, such as a heart, which is perfused with fluid, and cardiovascular flow generated therein. This can enable the testing of a medical device implanted in the organ under quasi-realistic conditions.

Therefore, simulation systems which can simulate a broad range of scenarios ranging from physiological cardiovascular flow to pathological cardiovascular blood flow are desirable. It is also desirable for simulation systems to be versatile and connectable to different types of test members, such as cadavers as well as cadaver body parts, organs, etc. However, it will be appreciated that different test members types can vary significantly from one another in terms of their flow path and the effect of the flow path on the overall fluid flow characteristics of the fluid flow circuit, in term of fluid path length, fluid flow resistance, etc. It will also be appreciated that within a test member type which are derived from a cadaver, originating different physiologies, state of the cardiovascular system, embalming technique if any, and presence of remaining blood clots will also give rise to a variation in flow path parameters.

Therefore, there is a desire for a simulation system that can overcome at least some of the above-described drawbacks.

SUMMARY

It is an object of the present technology to ameliorate at least some of the inconveniences present in the prior art.

Broadly, Developers have developed simulation systems which are connectable to test members of any type to create a fluid circuit and in which fluid circuit a desired target fluid profile can be induced, whether physiological or pathological. According to certain embodiments, the fluid flow profile induced in the fluid circuit can be easily modulated in real-time. In certain embodiments, simulation systems of the present technology can be connected to cadavers with a minimal number of connections.

Embodiments of the present technology can be used with test members of any non-viable form, for example: cadavers, cadaver body parts, cadaver organs, synthetic body parts, and synthetic organs. More specifically, test members may include cadaveric single organs, cadaveric vascular circuits between two points, whole cadaveric circuit, synthetic single organs, synthetic portions of organs (e.g. the left heart only) and synthetic vascular circuits (e.g. aorta to femoral arteries or any other circuit).

According to one aspect, there is provided a system for simulating cardiovascular fluid flow having a target fluid flow profile in a test member when connected thereto to form a fluid circuit, the system comprising: a reservoir for storing a fluid: a pump for pumping the fluid: an input channel fluidly connected to the reservoir at an input channel inlet and fluidly connectable to the test member at an input channel outlet, the input channel outlet configured to connect to the test member at a first position in the test member: an output channel fluidly connectable to the test member at an output channel inlet and fluidly connected to the reservoir at an output channel outlet, the output channel outlet configured to connect to the test member at a second position in the test member, such that when the input and output channels are connected to the test member, the system forms a fluid circuit with the test member: a first valve in the input channel, the first valve operable between an open configuration and a closed configuration for modulating fluid flow in the input channel: a second valve in the output channel, the second valve operable between an open configuration and a closed configuration for modulating fluid flow in the output channel: a processor communicatively connected to the first valve and to the second valve, wherein the processor is configured to control the first valve and the second valve to generate the target fluid flow profile. The pump may be fluidly connected to the reservoir.

From another aspect, there is provided a system for simulating a target fluid flow profile in a test member when connected thereto, the system comprising: a reservoir for storing a fluid: a pump for pumping the fluid: an input channel fluidly connected to the reservoir at an input channel inlet and fluidly connectable to the test member at an input channel outlet, the input channel outlet configured to connect to the test member at a first position in the test member: an output channel fluidly connectable to the test member at an output channel inlet and fluidly connected to the reservoir at an output channel outlet, the output channel outlet configured to connect to the test member at a second position in the test member, such that when the input and output channels are connected to the test member, the system forms a fluid circuit with the test member: at least one valve in the input channel and/or the output channel, the at least one valve operable between an open configuration and a closed configuration for modulating fluid flow in the input channel and/or the output channel: wherein the at least one valve is a proportional solenoid valve.

In certain embodiments, the target fluid flow profile comprises a target pulsatile flow component and a target systemic resistance component, and wherein the processor is configured to modulate the first valve to generate the target pulsatile flow component in the input channel, and to modulate the second valve to generate the target systemic pressure component.

In certain embodiments, the first and/or second valves are proportional solenoid valves. In certain embodiments, the first valve is a proportional solenoid valve, and the second valve is a solenoid on/off valve.

In certain embodiments, the target pulsatile flow component simulates blood flow during diastole and systole phases of a heart beat in a living human or animal.

In certain embodiments, the system further comprises a filter in one or more of the input channel and the output channel.

In certain embodiments, the system further comprises at least one sensor operatively connected to at least one of the input channel and the output channel, the at least one sensor configured to measure a fluid parameter of the fluid in the input channel and/or the output channel.

In certain embodiments, the at least one valve is communicatively connectable to the processor, and wherein the processor is configured to determine in real-time, from the measured fluid parameter whether the target fluid flow profile is achieved in the fluid flowing in the system, and if the target fluid flow profile is not obtained, to control one or both of the first valve and the second valve until the target fluid flow profile is achieved.

In certain embodiments, the processor is configured to apply control settings to at least one of the first valve and the second valve to achieve the target fluid flow profile, the control settings having been obtained by the processor through a closed loop test in which preliminary control settings were applied to at least one of the first valve and the second valve, obtaining input of a measured fluid flow profile using at least one sensor operatively connected to at least one of the input channel and the output channel, modulating the preliminary control settings until the target fluid flow profile is generated, and determining the modulated preliminary control settings as the control settings to apply.

In certain embodiments, the system further comprises a display communicatively connectable to the processor, the processor configured to cause a display on the display of at least one of: the target fluid flow profile, the target pulsatile flow, a measured pulsatile flow, the target systemic vascular resistance. The display may be on a mobile device such as a mobile phone or a tablet.

In certain embodiments, the first and second positions comprise, respectively, one or more of: an artery and a vein in the test member: an artery and an artery in the test member; and a vein and a vein in the test member.

In certain embodiments, the system further comprises the test member, the system being fluidly connected to the test member to form the fluid circuit. In certain embodiments, the test member is a cadaver, the first and second positions comprise an artery and a vein of the cadaver, and wherein the cadaver the input and the output channel are connected to the artery and vein respectively (or vice versa) and wherein the cadaver includes a flow path between the artery and the vein. In these embodiments, the artery and the vein of the cadaver have been surgically connected at one portion thereof, and at another portion thereof the artery and the vein are connected to the input and the output channels.

In certain embodiments, the pump comprises one or more of: a centrifugal pump, a positive displacement pump, a diaphragm pump or a peristaltic pump.

In certain embodiments, the system further comprises a pulsatile flow pump comprising: a chamber for receiving fluid from the reservoir, the chamber having a chamber inlet and a chamber outlet, the chamber outlet fluidly connectable to the input channel; an actuator operatively connected to the chamber and configured to modulate a pressure in the chamber, and a chamber outlet valve at the chamber outlet.

In certain embodiments, the actuator comprises a piston acting directly on the chamber or a pressurization device for modulating pressure in or on the chamber.

In certain embodiments, the system is connectable to a heart having an aorta, a left atrium and a left ventricle, wherein the input channel is connectable to the left atrium, and the output channel is connectable to the aorta.

In certain embodiments, the system is connectable to a heart having an aorta, an atrium and a ventricle, wherein the input channel is connectable to the left atrium, and the output channel is connectable to the aorta.

In certain embodiments, the system further comprises a pulsatile flow pump fluidly connectable to the ventricle of a heart for simulating a pumping action of the heart through pumping fluid into the heart, the pulsatile flow pump comprising a fluid chamber for receiving fluid and configured to be actuatable to modulate a pressure in the fluid chamber.

In certain embodiments, the target fluid pressure profile is a time varying fluid pressure profile, and optionally is one of a physiological blood pressure profile and a pathological pressure profile.

In certain embodiments, the system further comprises a ventilation system configured to ventilate a respiratory circuit of the cadaver.

From another aspect, there is provided a method for simulating cardiovascular blood flow having a target fluid flow profile in a test member when a perfusion system is connected to the test member to form a fluid circuit therewith, the method being executed by a processor communicatively coupled to: a first valve in an input channel of the perfusion system, the input channel configured to supply fluid to the test member when connected thereto, and a second valve in an output channel of the perfusion system, the output channel configured to receive fluid from the test member when connected thereto, the method comprising: obtaining input, by the processor, of the target fluid flow profile, the target fluid flow profile comprising a target pulsatile flow component and a target systemic resistance component; controlling the first valve to generate the target pulsatile flow component in the input channel based on a predetermined first valve parameter; and controlling the second valve to generate the target systemic resistance component based on a predetermined second valve parameter.

From a yet further aspect, there is provided a method for simulating a target fluid flow profile in test member when a perfusion system is connected to the test member to create a fluid circuit therewith, the method being executed by a processor communicatively coupled to: a first valve in an input channel of the perfusion system, the input channel configured to supply fluid to the test member when connected thereto, and a second valve in an output channel of the perfusion system, the output channel configured to receive fluid from the test member when connected thereto, the method comprising: obtaining input, by the processor, of the target fluid flow profile, the target fluid flow profile comprising a target pulsatile flow component and a target systemic resistance component; controlling, by the processor, the first valve based on a preliminary first valve parameter, and obtaining input from a sensor of a measured fluid flow parameter in the input channel; adjusting the preliminary first valve parameter until the measured fluid flow parameter corresponds to the target pulsatile flow component; controlling the second valve based on a second preliminary second valve parameter, and obtaining input from a sensor of a measured fluid flow parameter; and adjusting the second preliminary second valve parameter until the measured fluid flow parameter corresponds to the target systemic resistance component.

From another aspect, there is provided a method for simulating a target fluid flow profile in a test member when a perfusion system is connected to the test member to create a fluid circuit therewith, the method being executed by a processor communicatively coupled to a proportional solenoid valve in an input channel of the perfusion system, the input channel configured to supply fluid to the test member when connected thereto, the method comprising: causing, by the processor, the proportional solenoid to have a substantially open configuration to simulate a start of a systole phase of the target fluid flow profile, and to have a substantially closed configuration to simulate a peak arterial pressure of the systole phase.

In certain embodiments, at least one of the first valve and the second valve is a proportional solenoid valve and at least one of the first valve parameter and the second valve parameter is a voltage to be applied to the at least one of the first valve and the second valve.

In certain embodiments, the target fluid flow profile simulates blood flow during a systole phase and a diastole phase of a heart cycle, the processor configured to cause the first valve to: substantially open to simulate a start of the systole phase, and substantially closed to simulate a peak arterial pressure during the systole phase and before the diastole phase.

In certain embodiments, an interval between the first valve being substantially open and being substantially closed is determined according to a desired relative duration of the systole phase and the diastole phase in the target pulsatile flow.

In certain embodiments, an interval of the systole phase comprises (ratio of the desired relative duration of the systole and diastole phases)*(60/heart rate). In certain embodiments, an interval of the diastole phase comprises (1−(ratio of the desired relative duration of the systole and diastole phases))*(60/heart rate).

In certain embodiments, the method further comprises the processor causing the second valve to substantially close at the peak arterial pressure during the systole phase and before the diastole phase.

In certain embodiments, the method further comprises the processor determining the predetermined second valve parameter by modulating the second valve between being open and closed; obtaining measured values of the fluid flow while the second valve is modulated between being open and closed; and determining a given second valve parameter as being the predetermined second valve parameter when the target system resistance component is achieved.

In certain embodiments, the method further comprises the processor determining the predetermined first valve parameter by modulating the first valve between being open and closed; obtaining measured values of the fluid flow while the first valve is modulated between being open and closed; and determining a given first valve parameter as being the predetermined first valve parameter when the target pulsatile flow component is achieved.

In certain embodiments, the method further comprises causing, by the processor, to display on a display, communicatively coupled to the processor, at least one of: the target pulsatile flow component, and the target systemic resistance component.

In certain embodiments, the method further comprises detecting a fluid parameter in one or both of the input channel and the output channel, and causing, by the processor, to display on a display, communicatively coupled to the processor, the fluid parameter.

From a further aspect, there is provided a method for perfusing a fluid in a cadaver, the method comprising: connecting a first artery of the cadaver to an input channel of a system as described above; connecting a first vein of the cadaver to an output channel of the system; connecting a second artery of the cadaver to a second vein of the cadaver to create a fluid path of low resistance inside the cadaver; and starting perfusion of the cadaver through the input channel with a fluid.

In certain embodiments, the method further comprises increasing a pressure and flow rate of the fluid during perfusion until clots are flushed out from the cadaver. In certain embodiments, the method further comprises applying fluidic shock waves to the fluid during perfusion.

In certain embodiments, the method further comprises connecting one or more of (i) the artery to the input channel, and (ii) the vein to the output channel, using for example a cannula. In certain embodiments, the method comprises connecting the artery to the vein.

According to one aspect of the present technology, there is provided a system configured to perfuse a cardiovascular circuit with a predetermined fluid flow profile. The system includes a reservoir for storing a fluid, an input channel, an output channel and control elements. The input channel fluidly is connected to the reservoir at an input channel inlet, and fluidly connectable to the cardiovascular circuit at an input channel outlet. The input channel includes a first branch having a first branch outlet, and a second branch independent of the first branch, the second branch having a second branch outlet. The first branch outlet and the second branch outlet merge upstream of the input channel outlet. The output channel is fluidly connectable to the cardiovascular circuit, and fluidly connected to the reservoir. The control elements are for independently modulating a first fluid parameter in the first branch and a second fluid parameter in the second branch. The control elements are communicably connectable with a processor and configured to control the first and second fluid parameters to obtain the predetermined fluid flow profile at the input channel outlet to perfuse the cardiovascular circuit with the fluid according to the predetermined fluid flow profile.

In some embodiments, the system further includes the processor communicatively connected to the control elements.

In some embodiments, the system further includes one or both of a first feedback line fluidly connected to the first branch and to the reservoir, and a second feedback line fluidly connected to the second branch and to the reservoir.

In some embodiments, the perfusion further includes one or more of a first fluid sensor operatively connected to the first branch to measure the first fluid parameter, the first fluid sensor being communicatively connectable to the processor, a second fluid sensor operatively connected to the second branch to measure the second fluid parameter, the second fluid sensor being communicatively connectable to the processor, and a third fluid sensor operatively connected to the input channel downstream from the merged first and second branch outlets, the third fluid sensor measuring a third fluid parameter and being communicatively connectable to the processor.

In some embodiments, at least one of the first fluid parameter, the second fluid parameter and the third fluid parameter is one or both of fluid pressure and fluid flow rate. In embodiments in which the predetermined fluid flow profile is a physiological blood flow, any of the first fluid parameter, the second fluid parameter and the third fluid parameter may also reflect a heart rate of the cardiovascular circuit.

In some embodiments, the system further includes at least one pump operatively connected to the first and second branches, the at least one pump being configured to independently pump fluid from the reservoir to the first branch and to the second branch.

In some embodiments, the at least one pump is a centrifugal pump.

In some embodiments, the control elements include one or more of a first valve operatively connected to the first branch and communicatively connectable to the processor, the first valve being operable to modulate fluid flow from the first branch towards the input channel output, a second valve operatively connected to the second branch and communicatively connectable to the processor, the second valve being operable to modulate fluid flow from the second branch towards the input channel output.

In some embodiments, one or both of the first valve and the second valve is a solenoid valve.

In some embodiments, the system further includes one or both of: a first flow control valve operatively connected to the first branch and communicatively connectable to the processor, the first flow control valve being operable to modulate fluid flow from the first branch towards the input channel output, and a second flow control valve operatively connected to the second branch and communicatively connectable to the processor, the second flow control valve being operable to modulate fluid flow from the second branch towards the input channel output.

In some embodiments, at least one of the control elements is a third flow control valve operatively connected to the first feedback line and communicatively connectable to the processor, and at least one of the control elements is a fourth flow control valve operatively connected to the second feedback line and communicatively connectable to the processor.

In some embodiments, the input channel has a third feedback line fluidly connected to the input channel, downstream from the merged first branch outlet and the second branch outlet and to the reservoir.

In some embodiments, at least one of the control elements is a fifth flow control valve operationally connected to the third feedback and communicatively connectable to the processor.

In some embodiments, the system further includes a display communicatively connectable to the processor, the display being configured to present at least one of: the first fluid parameter, the second fluid parameter, and the predetermined fluid flow profile.

In some embodiments, the display is on a mobile device.

In some embodiments, the system further includes a filter in the output channel.

In some embodiments, the system further includes the cardiovascular circuit to which the system is fluidly connected to form a fluid circuit.

In some embodiments, the cardiovascular circuit includes blood vessels in a cadaver. In some embodiments, the cardiovascular circuit is a synthetic cardiovascular circuit. In some embodiments, the synthetic cardiovascular includes one or more of cadaveric organs, animal organs and synthetic organs.

In some embodiments, the input channel outlet is fluidly connected to an artery of the cadaver, and an output channel inlet is fluidly connected to a vein of the cadaver.

In some embodiments, the predetermined fluid pressure profile is a time varying fluid pressure profile, and optionally is one of a physiological blood pressure profile and a pathological pressure profile.

In some embodiments, the first branch is configured to induce a diastolic fluid pressure in the cardiovascular circuit, and the second branch is configured to induce a systolic fluid pressure in the cardiovascular circuit.

In another aspect of the present technology, there is provided a surgical simulation system including the system according to the above aspect or according to the above aspect and one or more of the above embodiments and a ventilation system configured to ventilate a respiratory circuit.

According to another aspect of the present technology, there is provided a system configured to simulate a predetermined heartbeat of a cardiovascular circuit. The system includes a reservoir for storing a fluid, an input channel, an output channel and control elements. The input channel fluidly is connected to the reservoir at an input channel inlet, and fluidly connectable to the cardiovascular circuit at an input channel outlet. The input channel includes a first branch having a first branch outlet, and a second branch independent of the first branch, the second branch having a second branch outlet. The first branch outlet and the second branch outlet merge upstream of the input channel outlet. The output channel is fluidly connectable to the cardiovascular circuit, and fluidly connected to the reservoir. The control elements are for independently modulating a first fluid parameter in the first branch and a second fluid parameter in the second branch. The control elements are communicably connectable with a processor and configured to control the first and second fluid parameters to obtain the predetermined heartbeat in the cardiovascular circuit.

In another aspect of the present technology, there is provided a method for perfusing a fluid in embalmed cadavers. The method includes performing a first arteriovenous (also known as arteriovascular) fistulae on the cadaver, performing a second arteriovenous fistulae on the cadaver, performing a third arteriovenous fistulae on the cadaver, connecting an input cannula in an artery of the cadaver, connecting an output cannula in a vein of the cadaver, connecting the input cannula to an input channel of the system, connecting the output cannula to an output channel of the system, starting perfusion with a fluid having a continuous low-pressure flow; increasing pressure and flow rate of the fluid and proceeding with a simulation session.

In some embodiments, the method further includes applying pulsatile shockwaves to the cardiovascular system.

In another aspect of the present technology, there is provided a method for perfusing a cardiovascular circuit with a predetermined fluid flow profile. the method is executed by a processor communicatively coupled to control elements of a perfusion system which is fluidly coupled to the cardiovascular system. The method includes obtaining input of a predetermined fluid flow profile, and causing control elements of the perfusion system to independently modulate a first fluid parameter in a first branch of an input channel of the perfusion system and a second fluid parameter in a second branch of the input channel of the perfusion system. The input channel is fluidly connected to a reservoir containing fluid at an input channel inlet, and fluidly connected to the cardiovascular circuit at an input channel outlet. The control elements are configured to control the first fluid parameter and the second fluid parameter to obtain the predetermined fluid flow profile at the input channel outlet to perfuse the cardiovascular circuit with the fluid according to the predetermined fluid flow profile.

In some embodiments, the method further including the processor, obtaining a detected fluid parameter of the fluid at the input channel outlet, and responsive to the detected fluid parameter not matching a desired fluid parameter according to the predetermined fluid flow profile, causing the control elements of the perfusion system to further modulate the first fluid parameter and the second fluid parameter until the detected fluid parameter generally matches the desired fluid parameter.

In some embodiments, the method further includes the processor, obtaining a detected fluid parameter of the fluid in the first branch, and responsive to the detected fluid parameter not matching a desired fluid parameter in the first branch, causing modulation of one or more of the control elements until the detected fluid parameter generally matches the desired fluid parameter.

In some embodiments, the method further includes the processor, detecting a detected fluid parameter of the fluid in the second branch, and responsive to the detected fluid parameter not matching a desired fluid parameter in the second branch, causing modulation of one or more of the control elements until the detected fluid parameter generally matches the desired fluid parameter.

In some embodiments, the method further includes the processor, obtaining a detected fluid parameter of the fluid at the input channel outlet, and responsive to the detected fluid parameter matching a desired fluid parameter according to the predetermined fluid flow profile, maintaining the first fluid parameter at a generally constant value; and modulating the second fluid parameter between a minimum and a maximum value.

In some embodiments, the method further includes causing operation of at least one pump to cause fluid to flow from the reservoir to one or both of the first branch and the second branch.

In some embodiments, the method further includes the processor, obtaining at least one of a detected fluid parameter of the fluid in the first branch, a detected fluid parameter of the fluid in the second branch, and a detected fluid parameter of the fluid at the input channel outlet. The method also includes, responsive to the at least one detected fluid parameter of the fluid in the first branch, in the second branch, at the input channel outlet not matching at least one desired fluid parameter according to the predetermined fluid flow profile, modulating control elements in at least one of a first feedback line, a second feedback line and a third feedback line until the at least one detected fluid parameter of the fluid in the first branch, in the second branch, and at the input channel outlet generally matches the at least one desired fluid parameter, and the predetermined fluid flow profile is achieved, the first feedback line being fluidly connected to the first branch, the second feedback line being fluidly connected to the second branch, and the third feedback line being fluidly connected to the input channel downstream from merged first and second branch outlets.

In some embodiments, the control elements include a first valve and a second valve. The method further includes causing, by the processor, to open or close one or both of the first and second valves based on a predetermined time, and responsive to the detected fluid parameter not matching a desired fluid parameter according to the predetermined fluid flow profile, causing the control elements of the perfusion system to further modulate the first fluid parameter and the second fluid parameter until the detected fluid parameter generally matches the desired fluid parameter.

In some embodiments, the method further includes causing, by the processor, a display communicatively coupled to the processor, to display at least one of the first fluid pressure, the second fluid pressure and the input fluid pressure and a predetermined fluid flow profile on a display.

In some embodiments, the predetermined fluid flow profile is a physiological blood pressure profile.

In some embodiments, the method includes causing, by the processor, a first valve operatively connected to the first branch of the system to block fluid flow, causing, by the processor, a second valve operatively connected to the second branch to block fluid flow, modulating, by the processor, a first control element in the first branch to obtain a first fluid pressure in the first branch, modulating, by the processor, a second control element in the second branch to obtain a second fluid pressure in the second branch, causing, by the processor, the second valve to open to allow fluid flow from the second branch towards the cardiovascular circuit, modulating, by the processor, the second control element to reduce the second fluid pressure, and causing, by the processor, the first valve to open while simultaneously causing the second valve to close to allow fluid flow from the first branch toward to the cardiovascular circuit.

In another aspect of the present technology, there is provided a system for perfusing a cardiovascular circuit with a predetermined fluid flow profile. The system includes a processor communicatively couplable to control elements of a perfusion system. The processor is configured to execute a method. The method includes obtaining input of a predetermined fluid flow profile, and causing control elements of the perfusion system to independently modulate a first fluid parameter in a first branch of an input channel of the perfusion system and a second fluid parameter in a second branch of the input channel of the perfusion system. The input channel is fluidly connected to a reservoir containing fluid at an input channel inlet, and fluidly connected to the cardiovascular circuit at an input channel outlet. The control elements are configured to control the first fluid parameter and the second fluid parameter to obtain the predetermined fluid flow profile at the input channel outlet to perfuse the cardiovascular circuit with the fluid according to the predetermined fluid flow profile.

In another aspect of the present technology, there is provided a system configured to perfuse an organ with a predetermined fluid flow profile. The system includes a reservoir, an input channel, an output channel and at least one control element. The reservoir is configured to store a fluid. The input channel is fluidly connected to the reservoir at an input channel inlet and fluidly connectable to the organ at an input channel outlet. The output channel is fluidly connectable to the organ at an output channel inlet and fluidly connected to the reservoir at an output channel outlet. The at least one control element is configured to modulate a first fluid parameter in at least one of the input and output channels, the at least one control element being communicably connectable with a processor and configured to control the first fluid parameter to obtain the predetermined fluid flow profile at the input channel outlet to perfuse the organ with the fluid according to the predetermined fluid flow profile.

In some embodiments, the organ is a synthetic organ.

In some embodiments, the organ is part of a cardiovascular circuit.

In some embodiments, the at least one control element comprises at least one proportional flow control valve operable between an open configuration and a closed configuration to modulate a fluid pressure in at least one of the input and output channels.

In some embodiments, the predetermined fluid flow profile is representative of diastole and systole phases of a heart beat.

In another aspect of the present technology, there is provided a method for perfusing an organ with a predetermined fluid flow profile. The method is executed by a processor communicatively coupled to control elements of a perfusion system. The perfusion system is fluidly coupled to the organ. The method includes obtaining input of a predetermined fluid flow profile, and causing at least one control element of the perfusion system to modulate an input fluid parameter in an input channel of the perfusion system. The input channel is fluidly connected to a reservoir containing fluid at an input channel inlet, and is fluidly connected to the organ at an input channel outlet. The at least one control element is configured to control the input fluid parameter to obtain the predetermined fluid flow profile at the input channel outlet to perfuse the organ with the fluid according to the predetermined fluid flow profile.

In some embodiments, the method further includes causing at least one control element of the perfusion system to modulate an output fluid parameter in an output channel of the perfusion system. The output channel is fluidly connected to the reservoir and to the organ. The at least one control element is configured to control the output fluid parameter to obtain the predetermined fluid flow profile at the input channel outlet to perfuse the organ with the fluid according to the predetermined fluid flow profile.

In some embodiments, the at least one control element is a proportional flow control valve operable between an open configuration and a closed configuration, the predetermined fluid flow profile corresponding to systole and diastole phases of a heart, the perfusion system being configured to induce desired systole and diastole pressures in the fluid in the organ.

In the context of the present specification, unless expressly provided otherwise, a computer system may refer, but is not limited to, an "electronic device", an "operation system", a "system", a "computer-based system", a "controller unit", a "control device", a "microcontroller", a "microprocessor", and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

As used herein, the term "and/or" is to be taken as specific disclosure of each of the two specified features or components with or without the other. For example "A and/or B"

is to be taken as specific disclosure of each of (i) A, (ii) B and (iii) A and B, just as if each is set out individually herein Implementations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects, and advantages of implementations of the present technology will become apparent from the following description, the accompanying drawings, and the appended claims.

BRIEF DESCRIPTION OF THE DRAWINGS

For a better understanding of the present technology, as well as other aspects and further features thereof, reference is made to the following description which is to be used in conjunction with the accompanying drawings, where:

FIG. 3B is a front elevation view of an output valve of the perfusion system of FIG. 3A in an adjusted configuration.

FIG. 3C is the schematic diagram of FIG. 2A, with an input valve of the perfusion system of FIG. 3A in open and closed configurations.

FIG. 3D is the schematic diagram of FIG. 2A, with the input and output valves being in open and closed configurations.

FIG. 14 is a flowchart of a method for perfusing a fluid in a target member using for example the perfusion system according to the present technology.

FIG. 15 is a flowchart of a method for perfusing a fluid in a target member using for example the perfusion system according to the present technology.

DETAILED DESCRIPTION

Figure 1:
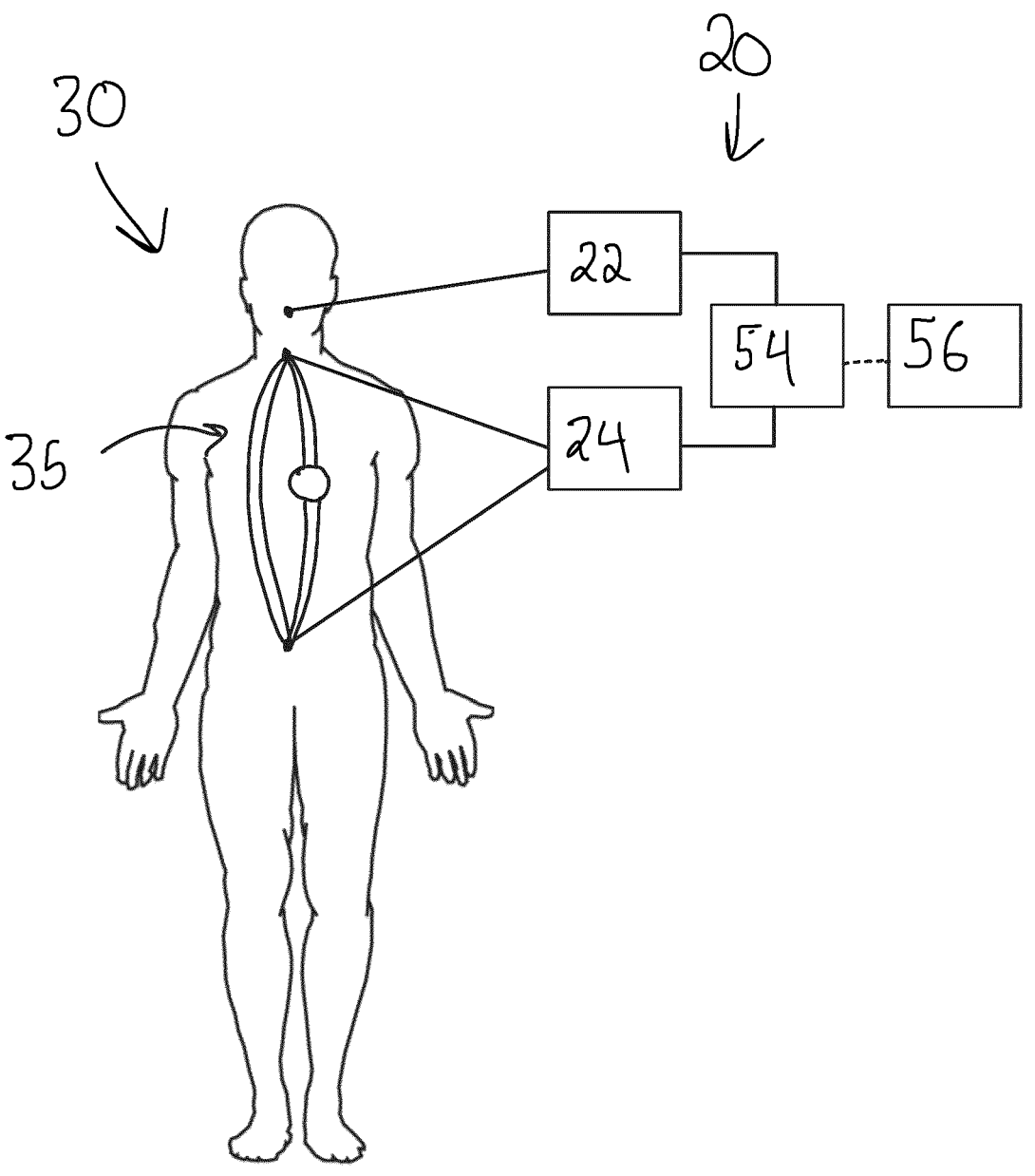
FIG. 1 is a schematic view of a simulation system connected to a cadaver, the simulation system including a perfusion system for simulating cardiovascular flow in a fluid to be perfused in the cadaver, a ventilation system for ventilating the cadaver and a processor, according to certain aspects of the present technology.

The present disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the following description, the same numerical references refer to similar elements.

Referring initially to FIG. 1, a simulator system 20 is shown fluidly connected to a test member 30. In the shown embodiment, the test member 30 is a cadaver 30. The cadaver 30 has been embalmed using standard embalming methods. In other embodiments, the cadaver 30 may have been embalmed using non-standard methods or be a fresh cadaver. In some embodiments, anticoagulants or clot-removing agents may have been used prior to or during embalmment. It is contemplated that in other embodiments, the simulator system 20 could be connected to a portion of a cadaver, such as certain organs. In other embodiments, the simulator system 20 can be connected to non-living anatomical systems such as human or animal dummies, or synthetic organs. Thus, the test member 30 could be a cadaveric single organ, a cadaveric vascular circuit between two points, a whole cadaveric circuit, synthetic single organs, and synthetic vascular circuits. In some embodiments, the test member 30 could be a kidney or a bladder. The test member 30 includes a flow path such as a cardiovascular circuit therein.

The simulator system 20 includes a perfusion system 24, and optionally a ventilation system 22. One or both of the ventilation system 22 and the perfusion system can be controlled by a same or different processor 54.

The ventilation system 22, when present, is connectable to a respiratory circuit of the cadaver 30 and is configured to perfuse the respiratory circuit with a gas, such as air, to simulate breathing. The ventilation system 22 comprises, in certain embodiments, a pressure regulator, pressure and flow sensors as well as a valve.

The perfusion system 24 is connectable to a flow path of the test member to create a fluid circuit therewith. The perfusion system 24 is configured to perfuse the fluid circuit with a fluid, such as a liquid, to simulate blood flow. The perfusion system 24 is configured to generate a target fluid low profile in the fluid, the target fluid flow profile having target fluid flow parameters such as a target pressure and/or target flow rate. In the case of the test member 30 being the cadaver, the flow path may comprise a cardiovascular circuit of the cadaver 30. When the simulator system 20 is connected to the cadaver 30, clinical conditions can be simulated, and thus the cadaver 30 can serve for training purposes, such as surgical training, or testing of medical devices, amongst other uses. In certain embodiments, the cardiovascular circuit may comprise an artery connected to a vein.

Although the perfusion system 24 is described as being part of the simulator system 20, and thus used in parallel with the ventilation system 22, it is contemplated that in some embodiments, the perfusion system 24 could be used alone (i.e., without the ventilation system 22). In other embodiments, there may be provided other systems to be used in parallel with the perfusion system 24.

Focusing on the perfusion system 24, and with reference to FIG. 3A, an embodiment of the perfusion system 24, namely perfusion system 24a, will now be described. The perfusion system 24a includes a reservoir 52, an input channel 60 fluidly connected to the reservoir 52 and fluidly connectable to the test member 30, an output channel 70 fluidly connectable to the test member 30 and fluidly connected to the reservoir 52. The perfusion system 24a also includes control elements, which will be described below, communicatively connected to the processor 54.

The reservoir 52 is configured to store a fluid, such as a mock blood solution, which has similar properties to blood (i.e. viscosity, coagulant properties, density, etc). It is contemplated that in other embodiments, the reservoir 52 could store other fluids. It is also contemplated that in some embodiments, there could be more than one reservoir. The reservoir may be generally vented.

The input channel 60 is fluidly connected to the reservoir 52 at an input channel inlet 62. The input channel 60 has an internal diameter of about 0.5 inches. Depending on the application of the perfusion system 24 (e.g., the type of test member 30 being perfused), it is contemplated that the internal diameter of the input channel 60 could increase to about 0.625 inches or about 0.75 inches. It is also contemplated that the internal diameter of the input channel 60 could decrease to about 0.375 inches.

The perfusion system 24a has a pump 64 operatively connected to the input channel 60) for pumping fluid from the reservoir 52 to the input channel 60. The pump 64 is a centrifugal pump. It is contemplated that in other embodiments, the pump 64 could be any other type of pump such as a positive displacement pump, or a peristaltic pump. In some embodiments, the pump 64 could have a one-way valve at an inlet of the pump 64 to avoid back flow. In some embodiments, the pump 64 could be configured to not be in direct contact with the fluid.

The perfusion system 24a further has an input valve 66 that is fluidly connected to the input channel 60 and that is communicatively connected to the processor 54. In the present embodiment, the input valve 66 is disposed downstream from the pump 64. The input valve 66 is operable between an open configuration and a closed configuration to modulate fluid flow in the input channel 60. It is to be noted that in the open configuration, the input valve 66 may be fully open, and in the closed configuration, the input valve 66 may be fully closed. However, it is contemplated that the open and closed configuration include any level of flow restriction between fully open and fully closed. For example, in the open configuration, the input valve 66 could be open at about 60% of its fully open configuration, and in the closed configuration, the input valve 66 could be open at about 10% of its fully open configuration. As will be described below, the extent of the fully open configuration can be used to modulate a fluid pressure in the perfusion system 24a. In some embodiments, the input valve 66 could be a proportional valve such as a solenoid valve (e.g. Type 2875, Burkert, Germany). An orifice size of the proportional solenoid valve to be used can be based on maintaining linearity between input electrical command signal (voltage and/or current and/or pulse-width modulated signal duty cycle) and output plunger position during use if desired, which can be easier to control, and can assist in avoiding discontinuities. However, non-linear uses of proportional solenoid valves are also contemplated. In yet other embodiments, the input valve 66 could be a motorized ball valve. It is contemplated that the input valve 66 could be configured to not have direct contact with the fluid (e.g., by contracting a tubing of the input channel 60), which can assist in extending a life of the input valve 66.

The input channel 60 is fluidly connectable to the test member 30 at an input channel outlet 68. Specifically, the input channel outlet 68 is configured to connect to the test member 30 at a first position of the test member 30. In some embodiments, the input channel outlet 68 could be connected to the test member 30 via a medical cannula. In some instances, a connector could be connected to the input channel outlet 68 to interface the cannula. In some embodiments, the connector could be used to make up for differences between internal diameters of the input channel outlet 68 and the medical cannula.

As mentioned above, the test member 30 could be a cadaveric organ, a synthetic organ, a whole cadaver, a portion of a cadaver, etc. It is contemplated that in some embodiments, the first position could be an artery of the test member 30. In other embodiments, the first position could be a vein of the test member 30. Furthermore, with reference to a larger circuit, such as when the test member 30 is a cadaver, it is contemplated that the first position could be in a femoral region, in a neck region or in a heart. In certain embodiments, the artery and the vein to which the input and output channels are connected, may themselves be surgically connected to form the fluid circuit. In other embodiments, the artery-vein connection could be made at another portion of the cadaver.

The output channel 70 is fluidly connectable to the test member 30 at an output channel inlet 72. Specifically, the output channel inlet 72 is configured to be connected to the test member 30 at a second position of the test member 30. It is contemplated that in some embodiments, the second position could be an artery of the test member 30. In other embodiments, the second position could be a vein of the test member 30. Furthermore, with reference to a larger circuit, such as when the test member 30 is a cadaver, it is contemplated that the second position could be in a femoral region, in a neck region or in a heart. In some embodiments, the output channel inlet 70 could be connected to the test member 30 via a medical cannula. In some instances, a connector could be connected to the output channel inlet 70 to interface the cannula. In some embodiments, the connector could be used to make up for differences between internal diameters of the output channel inlet 70) and the medical cannula.

The perfusion system 24a further has an output valve 76 that is in the output channel 70) and that is communicatively connected to the processor 54. The output valve 76 is operable between an open configuration and a closed configuration to modulate fluid flow in the output channel 62. It is to be noted that in the open configuration, the output valve 76 may be fully open, and in the closed configuration, the output valve 76 may be fully closed. However, it is contemplated that the open and closed configurations include any level of flow restriction between fully open and fully closed. For example, in the open configuration, the output valve 76 could be open at about 70% of its fully open configuration, and in the closed configuration, the output valve 76 could be open at about 20% of its fully open configuration. It is to be noted that the open and/or closed configurations of the output valve 76 could be different from the open and/or closed configurations of the input valve 66. In some embodiments, the output valve 76 could be a proportional valve such as a solenoid valve (e.g. Type 2875, Burkert, Germany). A size of the proportional solenoid valve to be used can be based on maintaining linearity if desired, which can be easier to control, and can assist in avoiding discontinuities. However, non-linear uses of proportional solenoid valves are also contemplated. In some embodiments, the output valve 76 could be on/off solenoid valve. In yet other embodiments, the output valve 76 could be a motorized ball valve. It is contemplated that the output valve 76 could be configured to not have direct contact with the fluid (e.g., by contracting a tubing of the output channel 70), which can assist in extending life of the output valve 76.

The input and output valves 66, 76 are configured to function independently of each other, and are configured to quickly and finely adjust from one configuration to the other. Though the input and output valves 66, 76 are illustrated herein as both being communicatively connected to the processor 54, it is understood that in other embodiments, each of the input and output valves 66, 76 could be connected to separate controllers.

Furthermore, in embodiments where at least one of the input and output valves 66, 76 is a solenoid valve, the at least one of the input and output valves 66, 76 is sized so that change in pressure therein is less than 25% of total pressure drop in the system. This can aid in maximizing a linearity of characteristics of the at least one of the input and output valves 66, 76. Additionally, the at least one of the input and output valves 66, 76 is sized so that change in pressure therein remains below 50% of the nominal pressure to avoid discontinuities. In some instances, the at least one of the input and output valves 66, 76 has an opening of about six millimeters. In other instances, the at least one of the input and output valves 66, 76 has an opening of about eight millimeters. In some embodiments, the size of the opening could vary according to the pump 64 used.

The output channel 70 is fluidly connected to the reservoir 52 at an output channel outlet 78.

Although not shown in this embodiment, it is contemplated that in some embodiments, the perfusion system 24a may have a filter connected to either one, or both, of the input and output channels 60, 70. The filter would filter fluid passing therethrough, and could capture debris and/or clots.

The perfusion system 24a further has a display 56 that is communicatively connected to the processor 54. The display 56 may be configured to be an input and output interface. In some embodiments, as will be described below, the display 56 could present information regarding the perfusion system 24a. The display 56 may comprise a mobile device, such as a mobile telephone, a tablet.

Figure 2A:
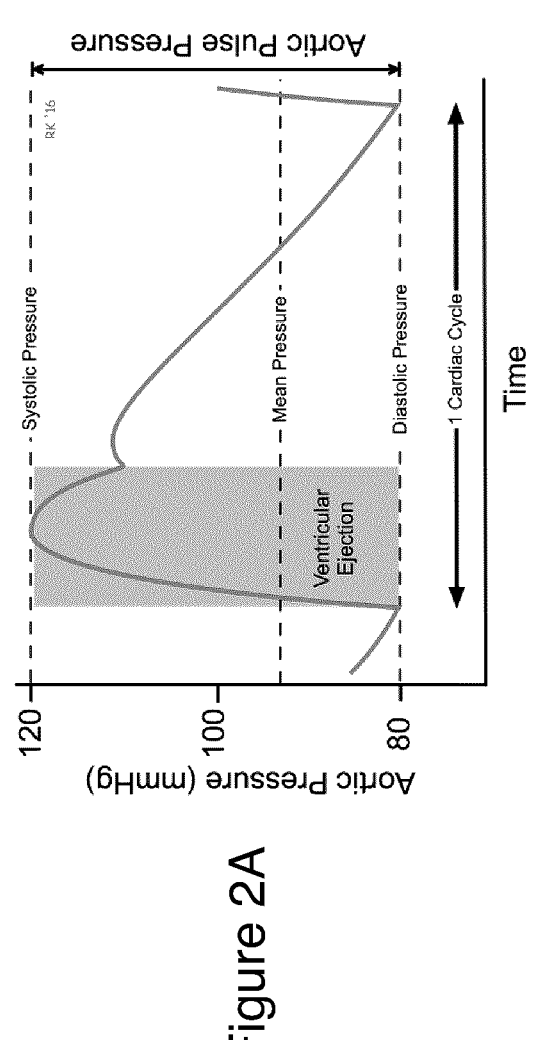
FIG. 2A is a schematic diagram illustrating an example of a target fluid flow profile to be induced in a target member, such as the cadaver of FIG. 1, by the perfusion system of FIG. 1, according to certain aspects of the present technology.
Figure 2B:
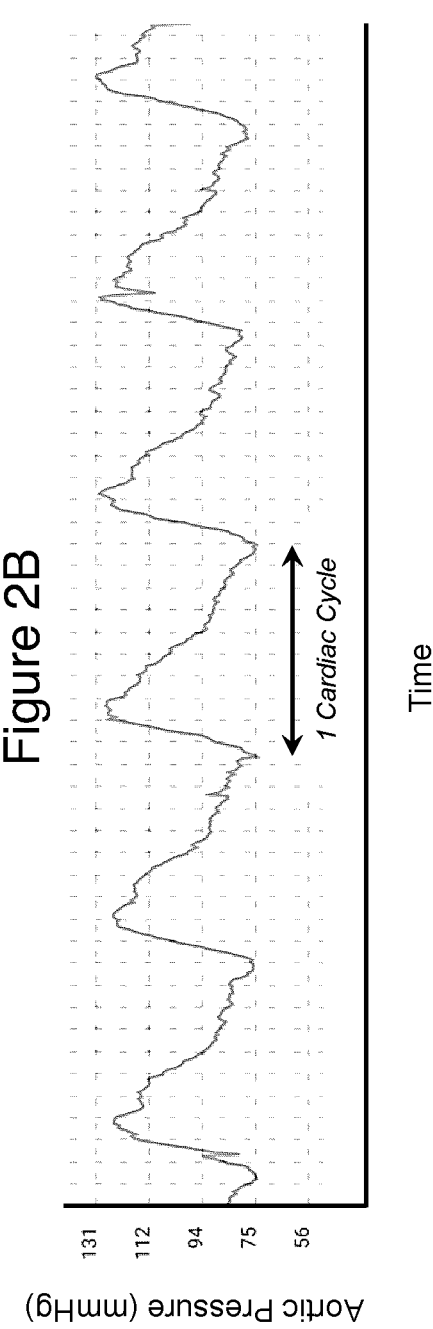
FIG. 2B is a schematic diagram illustrating an example of a recorded fluid flow profile induced in the target member of FIG. 1 by the perfusion system of FIG. 1, according to certain embodiments of the present technology.

The display 56 is configured to display target fluid flow parameters that can be modified by the user (heartrate, target pressures, target flowrate, target systolic/diastolic ratio, etc.) as well as measured values (flowrate, diastolic/systolic pressures, pressure curves, flowrate curves). The display 56 can also show graphs demonstrating the target and/or measured value parameters as shown in FIGS. 2A and 2B.

Figure 13:
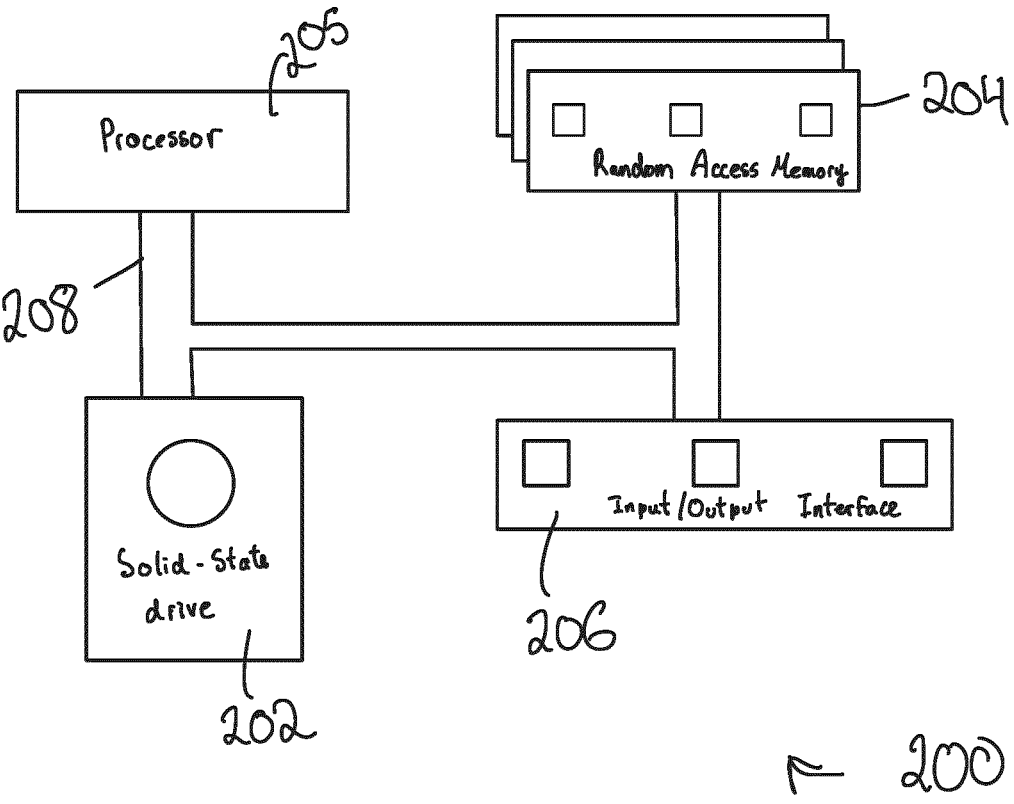
FIG. 13 is a schematic diagram of a computing environment of the processor of FIGS. 1, according to certain embodiments of the present technology.

With reference to FIG. 13, there is depicted a schematic diagram of a computing environment 200 suitable for use with some implementations of the present technology. The computing environment 200 includes various hardware components including one or more single or multi-core processors collectively represented by a processor 205, a solid-state drive 202, a random access memory 204 and an input/output interface 206. In some embodiments, the processor 205 could be the processor 105. Communication between the various components of the computing environment 200 may be enabled by one or more internal and/or external buses 208 (e.g. a PCI bus, universal serial bus, IEEE 1394 "Firewire" bus, SCSI bus, Serial-ATA bus, ARINC bus, I²C bus, CAN bus, etc.), to which the various hardware components are electronically coupled.

The input/output interface 206 allows enabling networking capabilities such as wire or wireless access. As an example, the input/output interface 206 includes a networking interface such as, but not limited to, a network port, a network socket, a network interface controller and the like. Multiple examples of how the networking interface may be implemented will become apparent to the person skilled in the art of the present technology. For example, but without being limiting, the input/output interface 206 may implement specific physical layer and data link layer standard such as Ethernet™, Fibre Channel, Wi-Fi™ or Token Ring. The specific physical layer and the data link layer may provide a base for a full network protocol stack, allowing communication among small groups of computers on the same local area network (LAN) and large-scale network communications through routable protocols, such as Internet Protocol (IP). As another example, in some embodiments, the input/output interface 206 could enable wireless communication of the processor 205 with at least one of the control elements by Bluetooth Low Energy (BLE), Bluetooth, Wifi.

According to implementations of the present technology, the solid-state drive 202 stores program instructions suitable for being loaded into the random access memory 204 and executed by the processor 205, according to certain aspects and embodiments of the present technology. For example, the program instructions may be part of a library or an application.

In some non-limiting embodiments of the present technology, the computing environment 200 is implemented in a generic computer system, which is a conventional computer (i.e. an "off the shelf" generic computer system). The generic computer system may be a desktop computer/personal computer, but may also be any other type of electronic device such as, but not limited to, a laptop, an integrated board featuring a microcontroller or a microprocessor, a mobile device, a smart phone, a tablet device, or a server. The computer system may include one or more of a keyboard and/or a mouse for receiving input from the user of the system 24 (such as the predetermined fluid pressure profile), a USB port, a microphone, a camera or the like.

As persons skilled in the art of the present technology may appreciate, multiple variations as to how the computing environment 200 can be implemented may be envisioned without departing from the scope of the present technology.

Referring back to FIG. 1, the perfusion system 24a has the display 56 for providing an input and/or an output to a user of the perfusion system 24a, the display 56 being in communication with the input/output interface 206. In some embodiments, the display 56 is embodied in a mobile device. In other non-limiting embodiments of the present technology, the display 56 may be a screen, a monitor, a speaker, a printer or embodied in any other device for providing an output in any form such as an image form, a written form, a printed form, an audio form, a 3D digital model form, or the like.

When the perfusion system 24a is connected to the test member 30, a fluid circuit 35 is formed with a test fluid circuit of the test member 30 such as one or more real or simulated blood vessels (e.g. a cardiovascular system of a cadaver: atrium/ventricles of a heart, etc.). The fluid circuit 35 can be perfused with the fluid. The perfusion system 24a is configured to induce a target fluid flow profile in the fluid of the fluid circuit 35. The target fluid flow profile can be predetermined, selected from a number of target fluid flow profiles or modulated live, as desired by an operator of the perfusion system 24. In some embodiments, the target fluid flow profile can be a physiological blood pressure profile or a pathological pressure profile. Thus, the perfusion system 24a is configured to simulate a desired fluid flow profile and can therefore model a patient-specific, condition-specific, scenario-specific or generic hemodynamic profile.

In some embodiments, the target fluid flow profile can be selected by the operator using the display 56, such as from one or more options presented to the operator on the display 56. Once selected, the processor can control one or both of the input and output valves 66, 76 to modulate between the open and closed configurations in order to reach the target fluid flow profile in the perfused fluid. In certain embodiments, the input valve 66 is modulated by the processor 56 to substantially control a fluid profile component of the target fluid flow profile (i.e. variation of fluid pressure with time within at least the input channel). The outlet valve 76 can be modulated by the processor 56 to model a desired cardiovascular systemic resistance. This can be particularly useful when the perfusion system is used with test members that are cadavers as a systemic resistance (i.e. resistance to fluid flow) of each cadaver can vary significantly between one cadaver and another cadaver. Therefore, the ability to achieve a desired systemic resistance despite a systemic resistance of the test member, provides great versatility.

Perfusion of the fluid circuit 35 by the perfusion system 24a will now be described. As mentioned above, the fluid perfusion is based on a target fluid flow profile. For the purposes of the present description, the target fluid flow profile is a physiological blood flow profile, is shown in FIG. 2A, that is observed in humans with physiologically relevant systolic and diastolic pressures. Although FIG. 2A illustrates the fluid flow profile over a single cardiac cycle, it will be appreciated that the induced pressure profile in the fluid of the fluid circuit 35 may include a sequence of cardiac cycles (as shown in FIG. 2B), the sequence of multiple cycles of the same profile or multiple cycles of different profiles.

The perfusion system 24a shown in FIG. 3 works as an open-loop system. As an open-loop system, the input and output valves 66, 76 are configured to be adjusted between their open and closed configurations based on timing ratios. It is understood that the restriction level at the open and closed configurations and/or the timing ratios could be changed for different target fluid flow profiles.

Figure 3A:
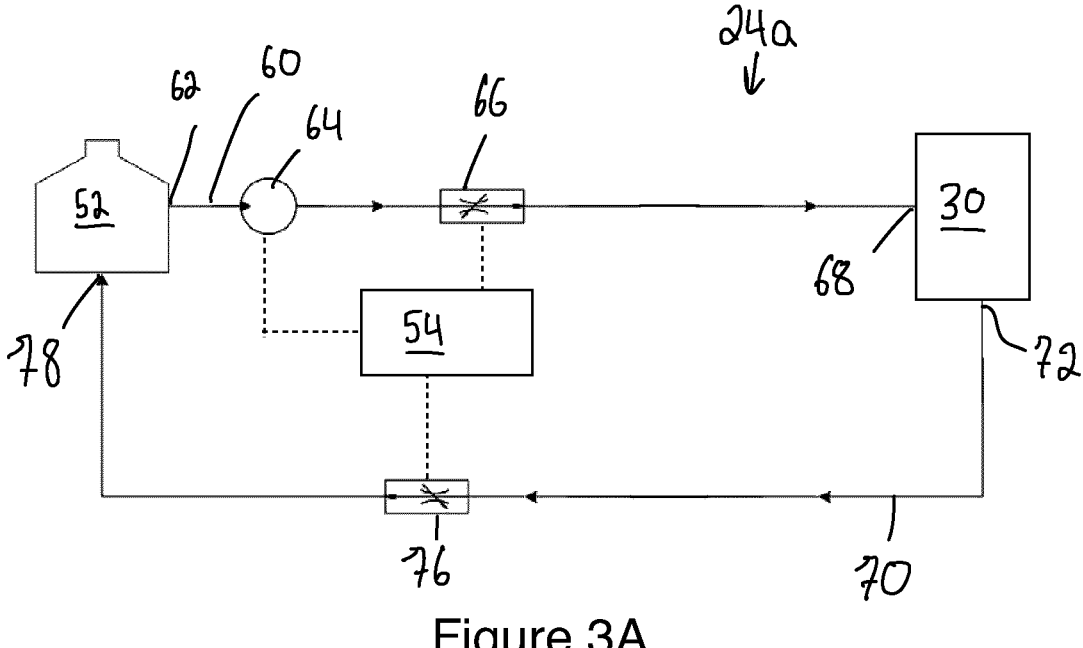
FIG. 3A is a schematic diagram of an embodiment of the perfusion system of FIG. 1 connected to a test member, according to certain embodiments of the present technology.

Referring to FIGS. 3A, 3B, 3C, to simulate the target fluid flow profile, a systemic vascular resistance is tuned by adjusting the opening of the output valve 76, as shown in FIG. 3B. The perfusion system 24a enables the adjustment of the systemic vascular resistance, which can be useful to simulate certain scenarios and/or to simulate a whole body cardiovascular circuit (i.e., adjusting the systemic vascular resistance to match the resistance of a whole body). Then, the input valve 66 is adjusted between the open and closed configurations. Specifically, at the beginning of the systole period, the input valve 66 is in the open configuration, as shown in FIG. 3C, which results in increasing pressure and flow, thereby provides the systole pressure spike. Then, the input valve 66 is adjusted to the closed configuration, which as shown in FIG. 3C, is not fully closed (i.e., the input valve 66 is in a constricted configuration). This results in slowing fluid flow, and decreasing pressure. The timing between the open and closed configurations is controlled by the systolic-to-diastolic time interval ratio of the desired target fluid flow profile, and is calculated based on parameters of the target fluid flow profile.

Referring to FIGS. 3D, another way of simulating the target fluid flow profile by the perfusion system 24a will be described. First, a systemic vascular resistance is tuned by adjusting the opening of the output valve 76, as shown in FIG. 3D. Then, at the beginning of the systole period, the input valve 66 is in the open configuration, as shown in FIG. 3D, which results in increasing pressure and flow, thereby provides the systole pressure spike. Then, the input and output valves 66, 76 are adjusted to their closed configurations, which as shown in FIGS. 3D, are not fully closed (i.e., the input and output valves 66, 76 are in a constricted configuration). This results in slowing fluid flow, and decreasing pressure, as shown in FIG. 2A. Additionally, flow at the output valve 76 is generally locked, and in instances where there is another branch, fluid flows therethrough. This can be useful when the test member 30 is a single heart with functional aortic valve, to obtain a flow in the coronary arteries. The timing between the open and closed configurations of the input and output valves 66, 76 are based on parameters of the target fluid flow profile.

Thus, in other words, when the perfusion system 24a functions as an open-loop system, a tuned series of commands are sent to the input and output valves 66, 76 from the processor to model the target fluid flow profile. The open-loop system can notably be useful when there is a desire to evaluate the impact of external devices and/or actions on the simulated cardiovascular system, such as, for instance, evaluating a surgeon's performance in a given scenario, or measuring the impact of an endoprosthesis on the cardiac output (flow rate of blood).

FIG. 2B shows an example of the measured fluid flow profile of the fluid perfused in the target member 30 by the perfusion system 24a.

Figure 4:
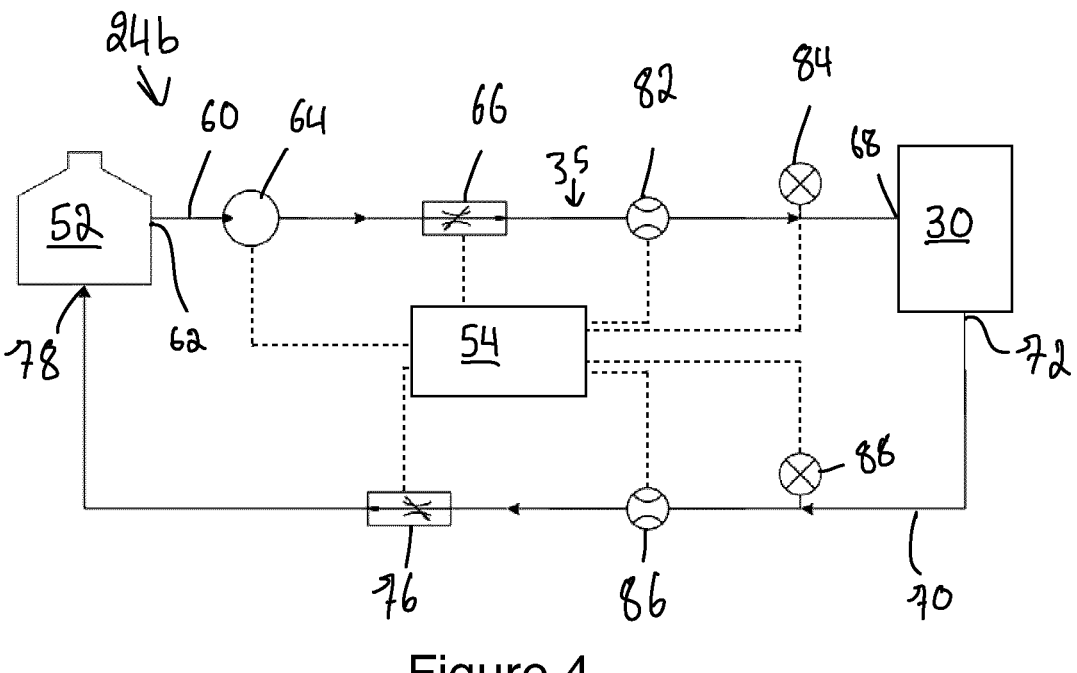
FIG. 4 is a schematic diagram of a perfusion system connected to a test member, according to certain embodiments of the present technology.

With reference to FIG. 4, an alternative embodiment of the perfusion system 24, namely perfusion system 24b, will now be described. Features of the perfusion system 24b similar to those of the perfusion system 24a have been labeled with the same reference numerals, and will not be described again.

The perfusion system 24b differs from the perfusion system 24a, in that there are additional control elements therein.

The perfusion system 24b includes an input flow sensor 82 that is operatively connected to the input channel 60, and that is communicatively connected to the processor 54. In the present embodiment, the input flow sensor 82 is disposed downstream from the input valve 66. The input flow sensor 82 is configured to sense the flow rate of the fluid at the input channel 60. The sensed flow rate is then communicated to the processor 54.

The perfusion system 24b further includes an input pressure sensor 84 that is operatively connected to the input channel 60, and that is communicatively connected to the processor 54. In the present embodiment, the input pressure sensor 84 is disposed downstream from the input valve 66. The input pressure sensor 84 is configured to sense the pressure of the fluid at the input channel 60. The sensed pressure is then communicated to the processor 54.

The perfusion system 24b further includes an output pressure sensor 88 that is operatively connected to the output channel 60, and that is communicatively connected to the processor 54. In the present embodiment, the output pressure sensor 88 is disposed upstream from the output valve 76. The output pressure sensor 88 is configured to sense the pressure of the fluid at the output channel 60. The sensed pressure is then communicated to the processor 54.

The perfusion system 24b further includes an output flow sensor 86 that is operatively connected to the output channel 70, and that is communicatively connected to the processor 54. In the present embodiment, the output flow sensor 86 is disposed upstream from the output valve 76. The output flow sensor 86 is configured to sense the flow rate of the fluid at the output channel 70. The sensed flow rate is then communicated to the processor 54.

It is contemplated that in other embodiments, there could be more or fewer sensors operatively connected to either one of the input and output channels 60, 70. For instance, in some embodiments, the input and output flow sensors 82, 86 could be omitted, such that the perfusion system 24b could only have the input and output pressure sensors 84, 88.

Additionally, all sensors 82, 84, 86, 88, can be chosen to avoid direct contact with the fluid (i.e., ultrasonic non-contact flow sensors, and diaphragm pressure sensors). In the present embodiment, the flow sensors are ultrasonic flow sensors. These flow sensors can have a precision of about 3 to 5%, and have a response time of about 100 ms. In the present embodiment, the pressure sensors are piezo-resistive pressure sensors, which have a precision of about 0.5%, and have a response time of about 1 millisecond. It is contemplated that in other embodiments, other types of sensors could be used to measure the same or other fluid parameters such as temperature, volume input, volume output.

In some embodiments, sensors could be placed inside the target member 30, such as by using pigtail pressure sensors inserted by catheter, or other similar components. This can provide an accurate direct measurement of the fluid flow profile within the target member 30.

The parameters measured by the sensors 82, 84, 86, 88, as mentioned above, are communicated to the processor 54. The processor 54, in turn, can cause the measured parameters to be displayed on the display 56. Thus, the display 56 could show real time readings of the fluid circuit 35 perfused by the perfusion system 24b.

Additionally, as will be described below, the sensors 82, 84, 86, 88 also enable the perfusion system 24b to work as a closed-loop system. As a closed-loop system, the input and output valves 66, 76 are configured to be modulated to their open and closed configuration in response to the fluid flow parameters measured by the sensors 82, 84, 86, 88. Specifically, the processor 54, based on the parameters measured by the sensors 82, 84, 86, 88 operates the input and output valves 66, 76 so that the measured parameters generally correspond to parameters of the target fluid flow profile. Thus, the input and output valves 66, 76 are configured to be dynamically controlled in real-time. More specifically, the processor 54 is configured to dynamically control the input and output valve 66, 76 including one or more of the following parameters: an extent of opening of the valve (e.g. fully open, partially open, fully closed, partially closed), and a rate of opening of the valve). It is contemplated that the input and output valves 66, 76 could be replaced by other flow control devices that permit to quick, precise and accurate adjustment of fluid flow.

Perfusion of the fluid circuit 35 by the perfusion system 24b will now be described, where the perfusion system 24b works as a closed-loop system. The systemic vascular resistance is tuned by adjusting the opening of the output valve 76. Then, the input valve 66 is adjusted to the open configuration, which results in increasing pressure and flow, thereby provides the systole pressure spike. The flow rate and pressure of the fluid at the input channel 60 are measured by the input flow and pressure sensors 82, 84, and communicated to the processor 54. In response to the parameters measured by the input flow and pressure sensors 82, 84, the processor 54 adjusts the opening of the input valve 66 as required to model the desired value of the flow rate and pressure.

It is understood that the same applies to the output valve 76. Thus, the processor 54 is configured to adjust the output valve 76 between the open and closed configurations in response to parameters measured by the flow rate and pressure sensors 86, 88.

Thus, in other words, when the perfusion system 24b functions as a closed-loop system, the processor 54 applies control settings to at least one of the input and output valves 66, 76 to achieve the target fluid flow profile. The processor 54 adjusts the input and output valves 66, 76 based on a fluid profile corresponding to the desired simulated hemodynamics. The flow and/or pressure sensors 82, 84, 86, 88 are used in a feedback loop of the processor 54 to enable the perfusion system 54 to continuously adapt the simulation model's variability, external disturbances, and more to robustly model the target fluid flow profile.

The perfusion system 24b working as a closed-loop system can notably be useful when there is need to rigorously model fluid profile, regardless of external disturbances, such as, for example, testing the structural integrity and fatigue performance of an aortic device when submitted to various hemodynamic profiles.

It is to be noted that the perfusion system 24b is selectively adjustable between an open-loop system and a closed-loop system. This can useful in various instances. In one such instance, it may desired to use the perfusion system 24b as a closed-loop system for a baseline setup. This could notably be useful when using cadavers or portions of cadavers due to variability between them. Once the baseline setup has been reached, the perfusion system 24b could selectively be adjusted to work as an open-loop system using the input and output valve control parameters established in the baseline setup phase. It is to be noted that the selective adjustment from the closed-loop system to the open-loop system could be done manually or automatically.

Figure 5:
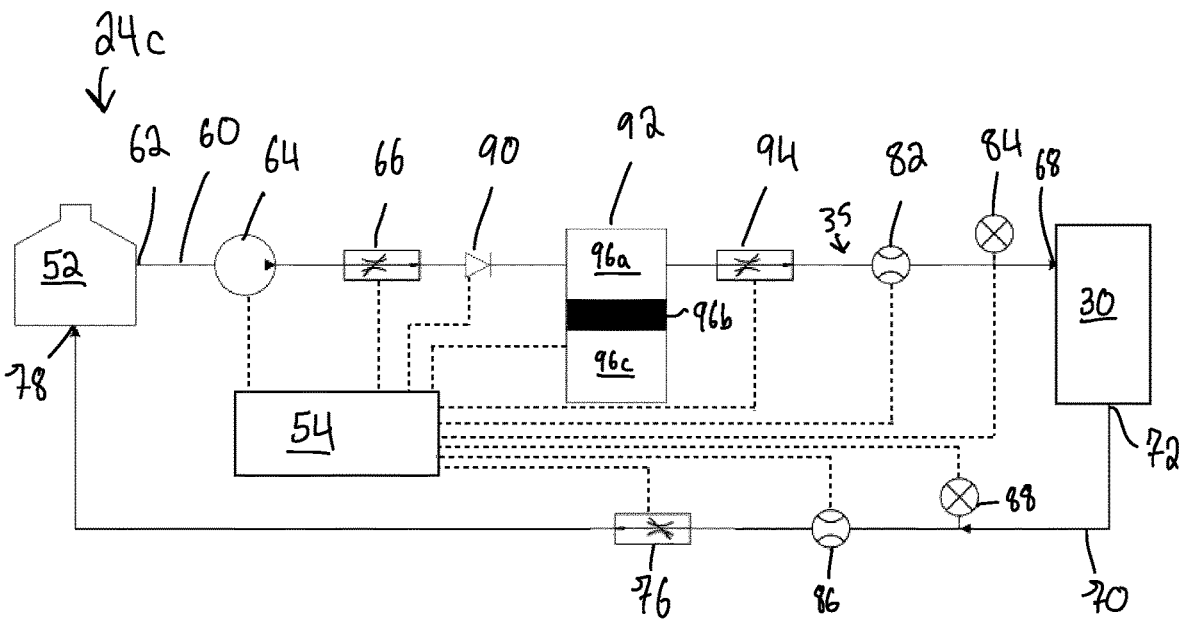
FIG. 5 is a schematic diagram of a perfusion system connected to a test member, according to certain embodiments of the present technology.

Referring to FIG. 5, an alternative embodiment of the perfusion system 24, namely perfusion system 24c, will now be described in greater detail. Features of the perfusion system 24c similar to those of the perfusion systems 24a, 24b have been labeled with the same references numerals, and will not be described in detail herewith.

The perfusion system 24c differs from the perfusion system 24a, in that it further includes a check valve 90, a pulsatile flow pump 92, and a secondary valve 94.

The check valve 90, which is disposed downstream from the pump 64 and the input valve 66, is for preventing backflow towards the pump 64. The check valve 90 is a mechanical one-way valve. It is contemplated that in other embodiments, the check valve 90 could be a on/off valve controller.

The pulsatile flow pump 92, which can assist in providing a more realistic perfusion of the fluid circuit 35, is disposed downstream from the check valve 90. The pulsatile flow pump 92 includes a chamber 96a, a piston 96b and an actuator 96c. The chamber 96a has a chamber inlet, and a chamber outlet, both of which are fluidly connected to the input channel 70. Additionally, the chamber 96a could come in various types such as a cylinder, a syringe, and/or a flexible pouch. The piston 96b, which can, in some instances, be referred to as a diaphragm, is configured to increase pressure in the chamber 96a (by reducing volume thereof). The actuator 96c is operatively connected to the piston 96b, and is configured to move the piston 96b so that the piston 96b can increase pressure in the chamber 96b. The actuator can be, for instance, a voice coil actuator, a moving coil, a moving magnet or a linear motor. The actuator 96c is communicatively connected to the processor 54. In some embodiments, the piston 96b could be omitted, and the actuator 96c could be directly increasing pressure in the chamber 96a by reducing volume thereof.

The secondary valve 94, which is disposed downstream from the pulsatile flow pump 92, is configured to control fluid flow therethrough. The secondary valve 94 could be a solenoid proportional valve, a solenoid on/off valve or even a custom check valve.

In operation, the pump 64 pumps the fluid from the reservoir 52. The input valve 66 can be controlled by the processor 54 to manage the flow rate output of the pump 64 in the event that the pump 64 cannot be controlled independently. Thus, in some embodiments, the input valve 66 could be omitted.

The flow then goes through the check valve 90 before entering the fluid chamber 96a through the chamber inlet. The fluid fills the fluid chamber 96a.

Then, in response to a command by the processor 54, fluid exits the fluid chamber 96a through the chamber outlet. Specifically, the processor 54 causes the actuator 96c to move the piston 96b such that a pressure thereof is increased, which results the fluid exiting the fluid chamber 96a.

Downstream from the fluid chamber output, the secondary valve 94 controls when the fluid is allowed to pass through.

Then, the fluid flows through the flow and pressure sensors 82, 84, through the test member 30, through the flow and pressure sensors 86, 88, through the output valve 76, and back to the reservoir 52.

Similarly to what was mentioned above with respect to the perfusion system 24b working as a closed-loop system, the measured parameters can be used by the processor 54 to adjust operation of the pump 64, the input valve 66, the pulsatile flow pump 92 and the secondary valve 94 to simulate a target fluid flow profile. In other words, timing of the opening and closing of the input and output valves 66, 76, the check valve 90, the secondary valve 94, as well as the speed of fluid ejection from the fluid chamber 96a by the piston 96b and the actuator 96c is controlled by the processor 54 based on the desired perfusion parameters, such as desired pressure profile, desired flow, heart rate, crisis scenario, etc.

A description of the perfusion system 24c perfusing the fluid circuit 35 with a target fluid profile will now be provided, where the target fluid profile, for the purposes of the present example, is the physiological blood flow profile shown in FIG. 2A.

In the diastole phase, the input valve 66 opens to a controlled level, and flows through the check valve 90 into the fluid chamber 96a. The actuator 96c causes the piston 96b to move toward a set receded position, thereby drawing in a physiological volume of the fluid into the fluid chamber 96c. The secondary valve 94 stays closed to keep the fluid inside the fluid chamber 96a.

In the systole phase, the input valve 66 closes to prevent fluid from further filling the fluid chamber 96a. The actuator 96c causes the piston 96b to move toward a set contracted position, thereby inducing a change of volume in the fluid chamber 96a corresponding to the desired ejection volume (about 70 milliliters as an average physiological value). This ejection volume can be controlled through the set receded and contracted positions of the piston 96b, depending on the perfusion parameters. The secondary valve 94 opens to allow fluid to flow out of the fluid chamber 96a. The check valve 90 upstream from the fluid chamber 96a prevents backflow towards the pump 64.

Figure 6:
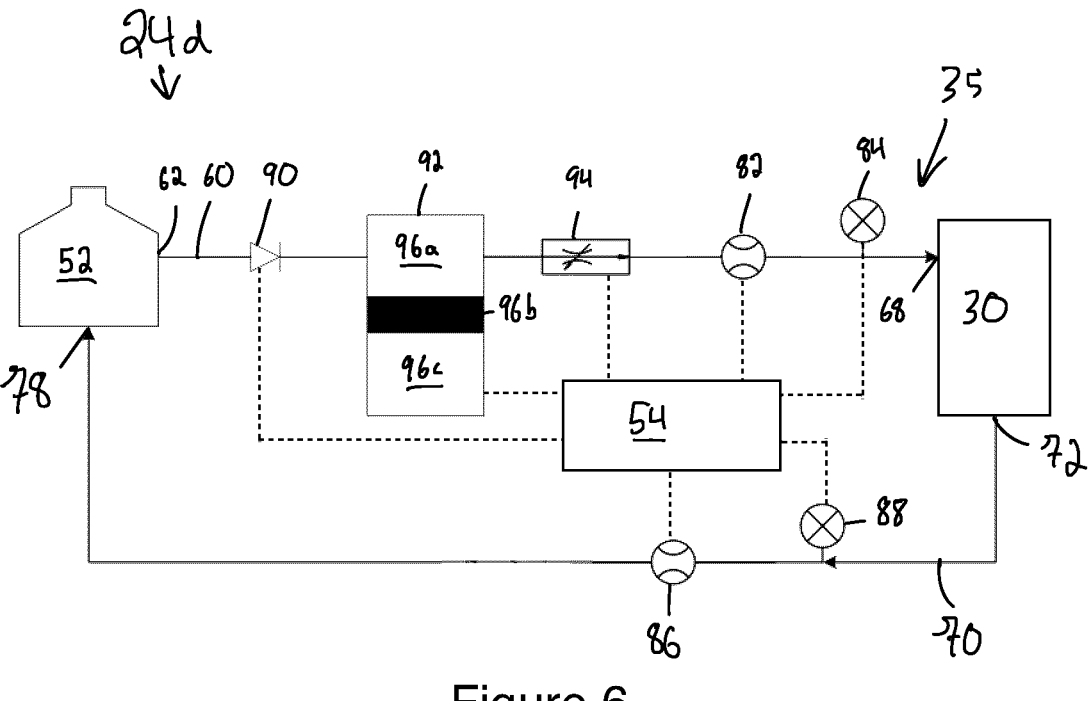
FIG. 6 is a schematic diagram of a perfusion system connected to a test member, according to certain embodiments of the present technology.

With reference to FIG. 6, an alternative embodiment of the perfusion system 24, namely perfusion system 24d, will now be described. Features of the perfusion system 24d similar to those of the perfusion systems 24a, 24b, 24c have been labeled with the same reference numerals, and will not be described again.

The perfusion system 24d differs from the perfusion system 24c in that the pump 64, the input valve 66, and the output valve 76 have been omitted. It is contemplated that in some embodiments, instead of omitting the input valve 66, the secondary valve 94 could be omitted, and the input valve 66 would be disposed downstream from the pulsatile pump flow 92. In this embodiment, fluid chamber 96a is filled with the fluid from the reservoir 52 by the piston 96b moving, in response to the actuator 86b, to a receded position. Movement of the piston 96b to the receding position induces a vacuum within the fluid chamber 96a that causes the check valve 90 to open, and causes fluid to be drawn from the reservoir 52 toward the fluid chamber 86a. The perfusion system 24d otherwise works similarly to the perfusion system 24c, and thus its operation will not be described in detail herewith.

Figure 7:
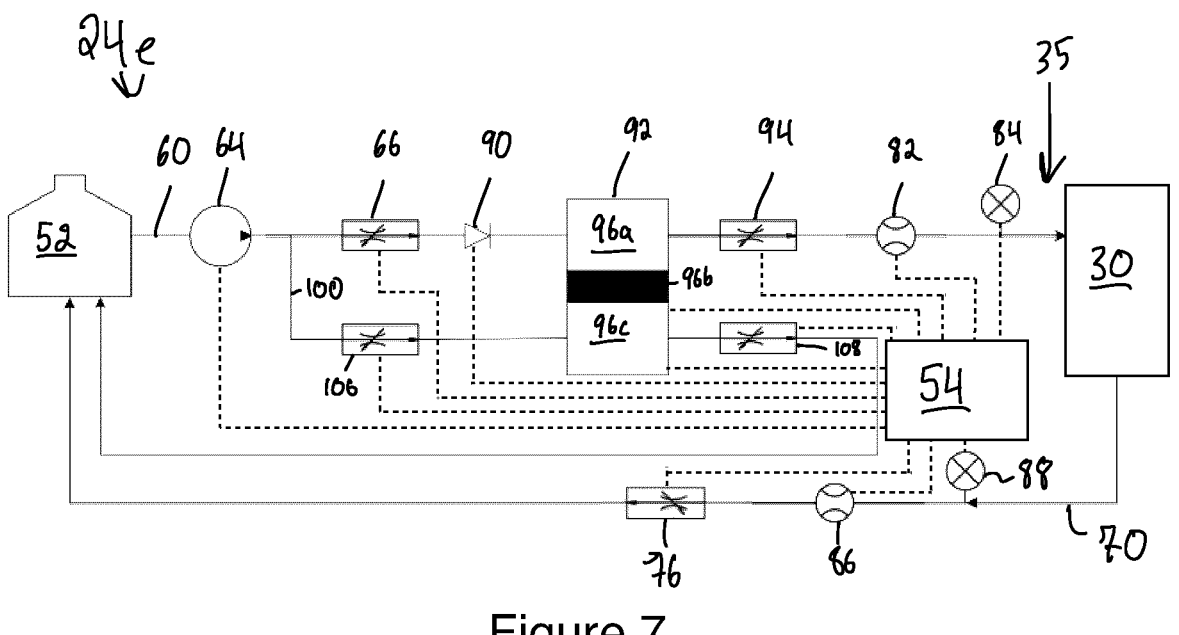
FIG. 7 is a schematic diagram of a perfusion system connected to a test member, according to certain embodiments of the present technology.

Referring to FIG. 7, an alternative embodiment of the perfusion system 24, namely perfusion system 24e, will now be described. Features of the perfusion system 24e similar to those of the perfusion systems 24a, 24b, 24c, 24d have been labeled with the same reference numerals, and will not be described again.

The perfusion system 24e differs from the perfusion system 24c in that the actuator 96c of the pulsatile flow pump 92 is an actuation chamber 96c, and in that the perfusion system 24e has a pressure channel 100.

The pressure channel 100 is fluidly connected to the input channel 60, downstream from the pump 64, is fluidly connected to the actuation chamber 96c by chamber inlet and outlet valves, and is fluidly connected to the reservoir 52.

The perfusion system 24e includes a pressure valve 106 operatively connected to the pressure channel 100 upstream from the actuation chamber 96c, and a secondary pressure valve 108 operatively connected to the pressure channel 100, downstream from the actuation chamber 96c.

In this embodiment, the piston 96b is moved by increasing pressure in the actuation chamber 96c. To do so, the input valve 66 is closed, the pressure valve 106 is opened and the secondary pressure valve 108 is closed. Then, fluid is pumped, by the pump 64, from the reservoir 52 to the actuation chamber 96c. Since flow out of the actuation chamber 96c is restricted, pressure in the actuation chamber 96c increases until it is greater than the pressure in the fluid chamber 96a, thereby causing that piston 96b to move. Thus, the perfusion system 24e can assist in reducing costs when compared with the perfusion system 24e by omitting an actuator, and instead using existing fluid circuit, and leveraging already present pressure controls to actuate the pulsatile flow pump 92.

A description of the perfusion system 25e perfusing the fluid circuit 35 with a target fluid profile will now be provided, where the target fluid profile, for the purposes of the present example, is the physiological blood flow profile shown in FIG. 2A.

For the diastole phase, the input valve 66 is adjusted to the open configuration, so that fluid can flow therethrough, through the check valve 90, and into the fluid chamber 96a. The secondary valve 94 stays closed to keep fluid within the fluid chamber 96a.

The secondary pressure valve 108 opens to release pressure inside the actuation chamber 96c, and pressure valve 96 closes to a level where the pressure differential between the fluid chamber 96a and the actuation chamber 96c (i.e., higher in the fluid chamber 96a) causes the piston 96b to move toward a receded position, allowing a physiological volume to fill the fluid chamber 96a.

Figure 8:
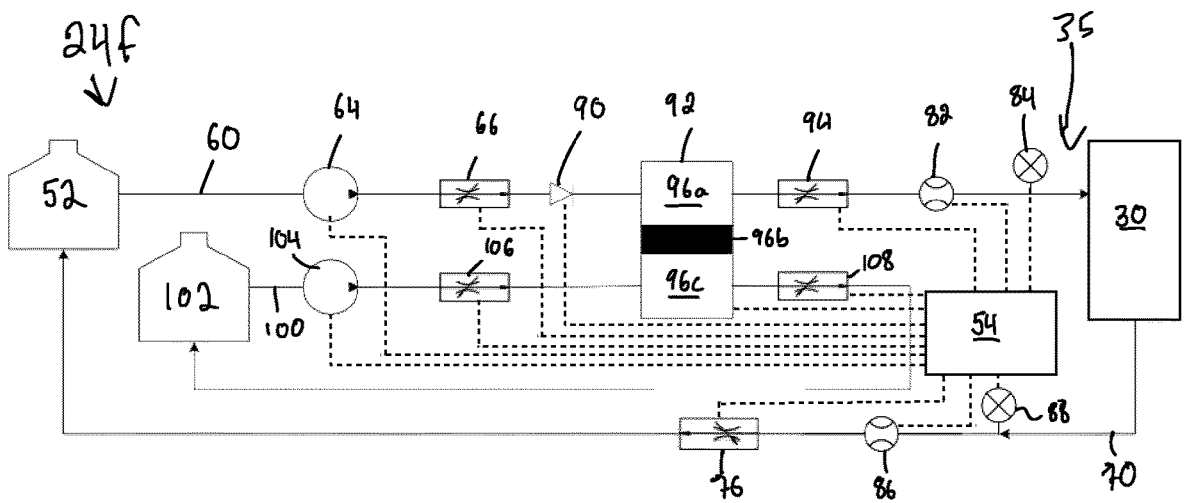
FIG. 8 is a schematic diagram of a perfusion system connected to a test member, according to certain embodiments of the present technology.

For the systole phase, the input valve 66 is adjusted to the closed configuration to prevent fluid from additionally filling the fluid chamber 96a. The secondary valve 94 is opened to allow fluid from the fluid chamber 96 to flow out thereof. The check valve 90 upstream from the fluid chamber 96a prevents backflow towards the pump 64. The secondary pressure valve 108 closes to pressurize the actuation chamber 96c, and the pressure valve 106 opens to a controlled level where the pressure differential between the fluid chamber 96a and the actuation chamber 96c (i.e., higher in the actuation chamber 96c) causes the piston 96b to move toward a contracted position, inducing a change of volume in the fluid chamber 96a corresponding to the desired ejection volume (about 70 milliliters as an average physiological value). This ejection volume can be controlled through the pressure differentials, depending on the perfusion parameters Referring to FIG. 8, an alternative embodiment of the perfusion system 24, namely perfusion system 24f, will now be described. Features of the perfusion system 24f similar to those of the perfusion systems 24a, 24b, 24c, 24d, 24e have been labeled with the same reference numerals, and will not be described again.

The perfusion system 24f is similar to the perfusion system 24e, except that a separate pressure fluid loop has been implemented for the actuation chamber 96c, with its own reservoir 102 and pump 104 (i.e., the pressure channel 100 is not fluidly connected to the input channel 60). This enables the use of a fluid different from the perfusion fluid to pressurize the actuation chamber 96c. Additionally, this permits the avoidance of the fluid that has travelled through the test member 30 (in case of multiple full cycles) from circulating in the actuation chamber 96c.

Figure 9:
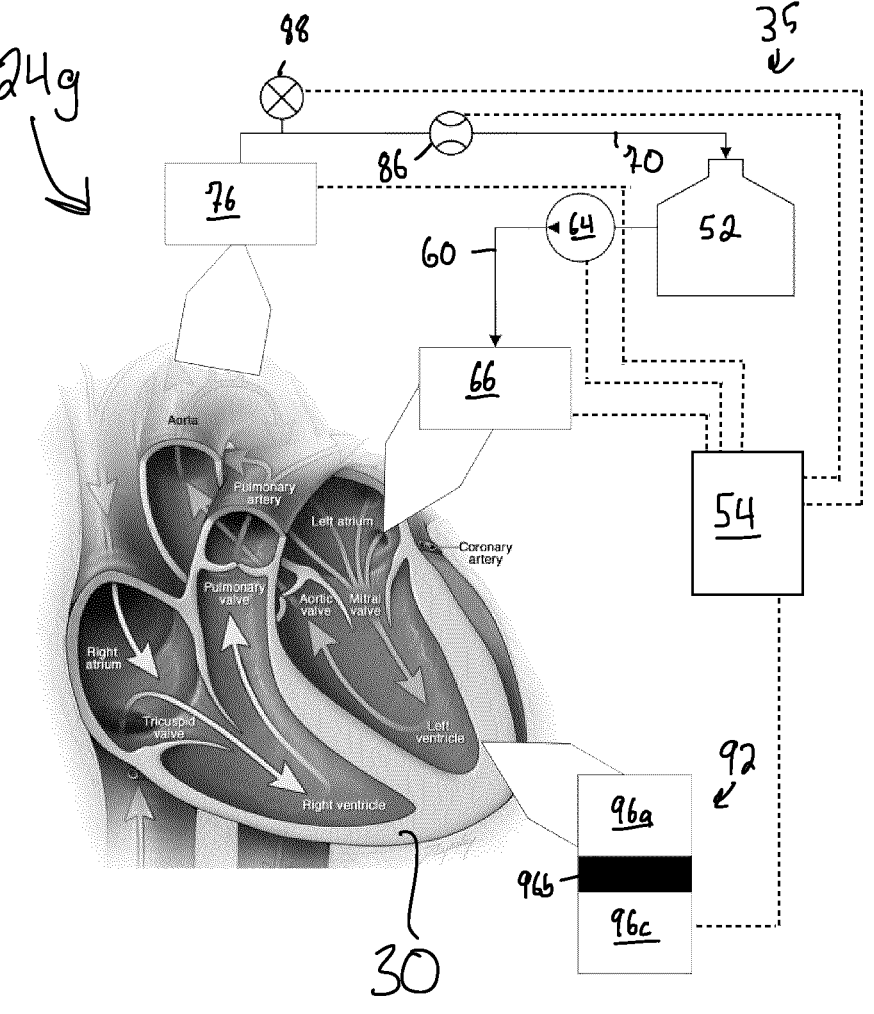
FIG. 9 is a schematic diagram of a perfusion system connected to a test member that is a heart, according to certain embodiments of the present technology.

With reference to FIG. 9, an alternative embodiment of the perfusion system 24, namely perfusion system 24g, will now be described. Features of the perfusion system 24g similar to those of the perfusion systems 24a, 24b, 24c, 24d, 24e have been labeled with the same reference numerals, and will not be described again.

In this embodiment, the test member 30 is a heart 30 (FIG. 9). In some embodiments, the heart 30 is a synthetic heart, and in other embodiments, the heart 30 is a cadaveric heart. In some embodiments, the heart 30 has functional anatomical valves. The heart 30 has an aorta, an atrium and a ventricle.

The perfusion system 24g includes the reservoir 52, the input channel 60, the pump 64, the input valve 66, the output channel 70, the output valve 76 and the flow and pressure sensors 86, 88. The perfusion system 24g further has the pulsatile flow pump 92. In the present embodiment, the pulsatile flow pump 92 includes the fluid chamber 96a, the piston 96b and the actuator 96c. It is contemplated that in some embodiments, the pulsatile flow pump 92 could be connected to a pressure circuit, as described hereabove with reference to the perfusion system 25f.

The input channel 60 is connected to the atrium, the output channel 70 is connected to the aorta, and the pulsatile flow pump 92 is connected to the ventricle.

A brief description of the perfusion system 25g perfusing the heart 30 with a target fluid profile will now be provided, where the target fluid profile, for the purposes of the present example, is the physiological blood flow profile shown in FIG. 2A.

For the diastole, the input valve 66 is opened to a set level, allowing fluid to flow therethrough, inside the atrium and ventricle. Specifically, in the present embodiment, the fluid flows inside the left atrium and the left ventricle. If a mitral valve is present in the perfused heart model, the mitral valve will naturally be open. The actuator 96c is configured to enable the piston 96b to move toward the receded position, thereby allowing fluid from the left ventricle to fill the fluid chamber 96a. When the piston 96b moves toward the receded position, fluid coming from the left atrium is drawn, and fluid in the aorta is also drawn, thereby closing the aortic valve, if present, through a backflow, and perfusing the coronary arteries.

For the systole, the input valve 66 closes, thereby preventing additional fluid from filling the ventricle. The actuator 96c causes the piston 96b to move toward a contracted position, which pushes a physiological controlled volume of fluid out into the ventricle, thereby opening the aortic valve because of the spike in pressure in the ventricle, and closing the mitral valve if present. Fluid flows into the aorta and the rest of the circuit.

In both systole and diastole, the output valve 76 can be adjusted to control the pressure in the aorta. It is contemplated that in some embodiments, the output valve 76 could be removed.

If the heart 30 does not include working anatomical valves, their action can be mimicked by controlling the opening and closing of the input and output valves 66, 76. In diastole, the input valve 66 would open, and the output valve 76 would close (same as the mitral valve, and the aortic valve respectively). In systole, the input valve 66 would close, and the output valve 76 would open. This enables the perfusion system 24g to simulate the pressure differentials, and realistic cardiac function in many different types of synthetic or cadaveric models.

In some embodiments, fluid can then continue in the circuit if arteries or veins are connected to the heart 30 or be directly recirculated toward the reservoir 52.

In some embodiments, the pump 64 may be omitted so that the pulsatile flow pump 92 would replace the pumping action of the pump 64 by creating a vacuum in the fluid chamber 96a in response to the actuator 96c moving the piston 96b to a receded position during diastole.

Figure 10:
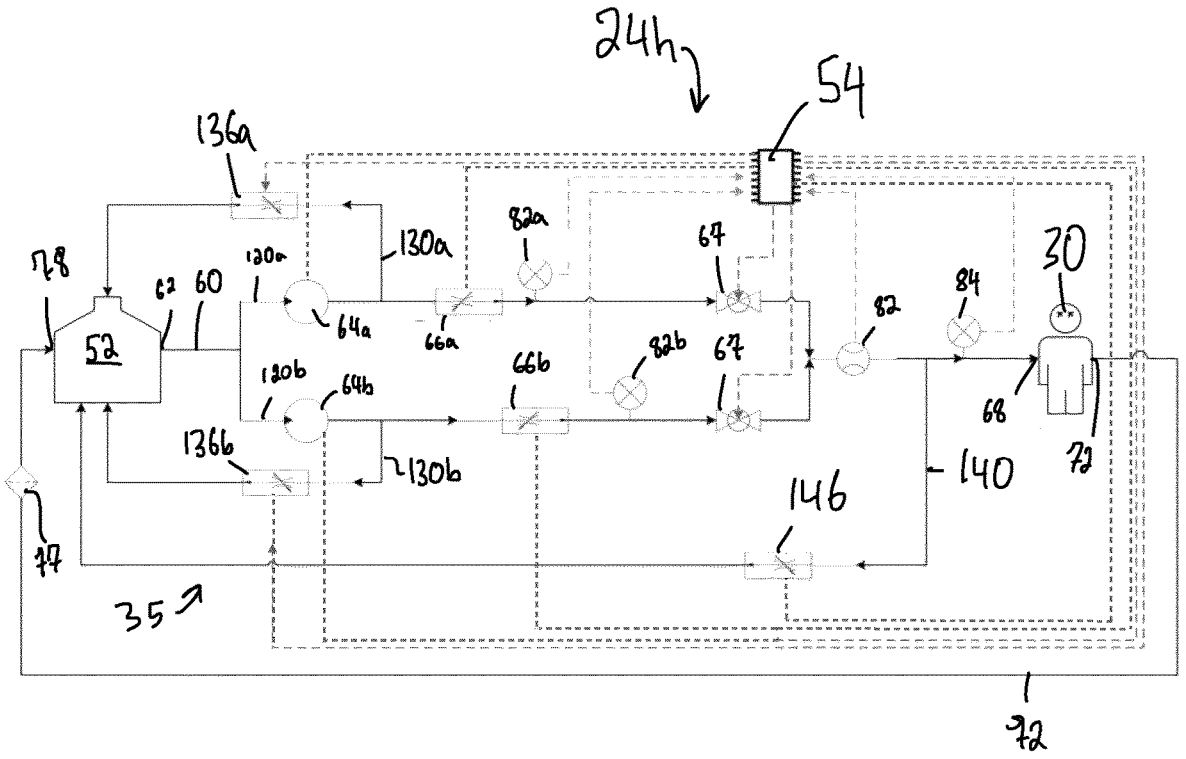
FIG. 10 is a schematic diagram of a perfusion system connected to a test member, according to certain embodiments of the present technology.

Referring now to FIG. 10, an alternative embodiment of the perfusion system 24, namely perfusion system 24h, will now be described. Features of the perfusion system 24h similar to those of the perfusion system 24a, 24b, 24c, 24d, 24e, 24f, 24g have been labeled with the same reference numerals and will now be described in detail again herewith.

Thus, the perfusion system 24h which is configured to perfuse the target member 30, includes the reservoir 52, the input channel 60, the output channel 70, control elements which will be describe below; and the processor 54.

In this embodiment, the input channel 60 is fluidly connected to the reservoir 52 at an input channel inlet 62. Downstream from the input channel inlet 62, the input channel 60 branches into branch 120a and branch 120b, which eventually merge back together. The branches 120a, 120b are independent of one another. It is contemplated that in some embodiments, each of the branches 120a, 120b could be directly connected to their respective reservoirs.

The branch 120a has a pump 64a similar to the pump 64, an input valve 66a similar to the input valve 66, a pressure sensor 82a similar to the pressure sensor 82, and a valve 67a similar to the input valve 66. The pressure sensor 82a is disposed downstream from the pump 64a and the input valve 66a. It is contemplated that in other embodiments, the pressure sensor 82a could be another fluid sensor such as flow sensor. A feedback line 130a is fluidly connected to the branch 120a downstream from the pump 66a and to the reservoir 52. A feedback valve 136a is operatively connected to the feedback line 130a. The feedback valve 136a is similar to the input valve 66.

Similarly, the branch 120b has a pump 64b similar to the pump 64, an input valve 66b similar to the input valve 66, a pressure sensor 82b similar to the flow sensor 82, and a valve 67b similar to the input valve 66. The pressure sensor 82b is disposed downstream from the pump 64b and the input valve 66b. It is contemplated that in other embodiments, the pressure sensor 82b could be another fluid sensor such as flow sensor. A feedback line 130b is fluidly connected to the branch 120b downstream from the pump 66b, and to the reservoir 52. A feedback valve 136b is operatively connected to the feedback line 130b. The feedback valve 136b is similar to the input valve 66.

Downstream from the valves 67a. 67b, the branches 120a, 120b merge. More precisely, a branch outlet 128a of the branch 120a merges with a branch outlet 128b of the branch 120b.

It is contemplated that in some embodiments a single pump could be configured to independently pump fluid from the reservoir 52 to the branches 120, 140. In some embodiments, the single pump could have two one-way valves after separation of the branches 120, 140.

The flow sensor 82 is operatively connected to the input channel 60, downstream from the merged branch outlets 128a, 128b.

A feedback line 140 is fluidly connected to the input channel 60, downstream from the flow sensor 82, and thus downstream from the merged branch outlets 128a, 128b. The feedback line 140 is also fluidly connected to the reservoir 52. A flow control valve is 146, which is similar to the input valve 66, is operatively connected to the feedback line 164.

Downstream from the connection between the feedback line 140 and the input channel 60, the pressure sensor 84 is operatively connected to the input channel 60.

As mentioned above, the pumps 66a, 66b, the valves 66a, 66b, 67a, 67b, 136a, 136b, 146a, 146b, the sensors 82a, 82b, 82, 84, which are communally referred to as control elements, are communicatively connected to the processor 54.

The input channel 60 is fluidly connected to the test member 30 at an input channel outlet 68.

In the present embodiment, the test member 30 is a cadaver 30, and includes includes blood vessels of the cadaver 30. More precisely, the input channel outlet 68 is fluidly connected to an artery of the cadaver 30. The fluid connection to the artery may be in a femoral region, in a neck region or in a heart of the cadaver 30. In other embodiments, the input channel outlet 68 could be connected to a vein of the cadaver 30.

The output channel 70 is fluidly connectable to the test member 30 at an output channel inlet 72. More precisely, the output channel inlet 72 is fluidly connected to a vein of the cadaver 30. In some embodiments, the vein could be the jugular vein. The fluid connection to the vein may be in a femoral region, a neck region of the cadaver 30, or any other suitable region of the cadaver 30. The cardiovascular circuit 62 of the cadaver 30 may include arteriovenous fistulae.

The output channel 70 includes a filter 77 configured to filter the fluid flowing therein. The output channel 70 is fluidly connected to the reservoir 52 at the output channel outlet 78.

When the perfusion system 24 is connected to the target member 30, the fluid circuit 35 is formed. In certain embodiments, the fluid circuit 35 enables fluid to flow from the reservoir 52, into the input channel 60, into the artery of the cadaver 30, where the fluid will flow through the cardiovascular system of the cadaver (e.g. aorta, heart, vein) and back into the perfusion system 24 via the output channel inlet 72 and back to the reservoir 52.

It is understood that in some embodiments, the perfusion system 24h could be different from the one described herein. For instance, in some embodiments, one or more of the feedback lines 130a, 130b, 140 could be omitted.

In certain embodiments, the perfusion system 24h is configured to induce the cardiovascular system with a predetermined pressure profile (i.e., target pressure profile), such as that shown in FIG. 3. As described above, the predetermined pressure profile of FIG. 3 simulates a physiological blood pressure pattern observed in humans with physiologically relevant systolic and diastolic pressures.

The perfusion system 24 also includes the display 56. As mentioned above, in some embodiments, the display 56 presents fluid parameters measured by the sensors 82a, 82b, 82, 84 and/or presents other information such as the predetermined pressure profile, number of cycles, etc.

Perfusion of a fluid in the target member 30 by the perfusion system 24 will now broadly be described. The fluid perfusion is based on the target fluid flow profile, which for the purpose of the present broad description, is the physiological blood flow profile illustrated in FIG. 3. In the present embodiment, the branch 120a is configured to induce a diastolic fluid pressure in the target member 30. Thus, the fluid pressure in the branch 120a will henceforth be referred to diastolic pressure. The branch 120b is configured to induce a systolic fluid pressure in the target member 30. Thus, the fluid pressure in the branch 120b will henceforth be referred to systolic pressure.

The pump 66a pumps fluid from the reservoir 52 to the branch 120a, and then the flow control valves 66a, 136a along with the pressure sensor 82a, regulate and keep the diastolic pressure at a predetermined value. The feedback line 130a aids in keeping the diastolic pressure at the predetermined value, even when disruptions can occur, for instance when the valve 67a opens.

Similarly, the pump 66b pumps fluid from the reservoir 52 to the branch 120b, and then the flow control valves 66b, 136b and the pressure sensor 82b regulate the systolic pressure. The feedback line 130b aids in regulating the systolic pressure. For instance, systolic pressure is configured to not exceed a maximal chosen systolic pressure thanks to the feedback line 130b. The maximal chosen systolic pressure is greater than the diastolic pressure.

At the beginning of the systole, the systolic branch 120b is at the maximal chosen systolic pressure. The valve 67b opens to simulate rapid ventricular ejection profile, as shown in FIG. 2A, and fluid flows from the systolic branch 120b toward the input channel outlet 68. At this stage, the fluid pressure at the input channel outlet 68, and thus the cardiovascular circuit of the target member 30, generally corresponds to the systolic pressure.

Then, the flow control valve 66b gradually closes, and the flow control valve 136b partly opens. This results in reducing the systolic pressure, which in turn reduces the pressure at the input channel outlet 68. In some embodiments, the flow control valve 66b and the flow control valve 136b could be timed to, respectively, close and open. In some embodiments, the flow control valve 66b and the flow control valve 136b could close and open at approximately 15% of the length of the cardiac cycle. In other embodiments, the length of closing/opening could be about 10%, about 20%, or about 25% of the length of the cardiac cycle.

Then, the valve 67b closes, and simultaneously, the valve 67a opens. In some embodiments, the valve 67b could close and the valve 67a could open when the systolic pressure reaches a minimal value. In other embodiments, the valve 67b and the valve 67a could be timed to, respectively, close and open. In some embodiments, the valve 67b could close, and the valve 67a could open at approximately 31% of the length of the cardiac cycle. In other embodiments, the valve 67b could close, and the valve 67a could open at approximately 20%, 25%, 30%, 35% or 40% of the length of the cardiac cycle. In embodiments where a timing of the valves 67a, 67b is modulated, at least some of the control elements can be operated to make fluid pressures in the systolic and diastolic branches 120a, 120b match their desired values. Thus, fluid flow from the systolic branch 120b stops, whereas fluid flow from the diastolic branch 120a starts flowing toward the input channel outlet 68. As the minimal value of the systolic pressure is greater than the diastolic pressure, this results in the pressure at the input channel outlet 68 dropping.

While the pressure at the input channel outlet 68 is dropping (i.e. during diastole), the flow control valve 66b opens, and the flow control valve 136b closes to increase the systolic pressure back toward the maximal pressure for another cardiac cycle. Then, the valve 67a closes, and the valve 67b opens, thereby restarting the cardiac cycle. It is contemplated that in some embodiments, the valve 67a could close, and the valve 67b could open when the fluid pressure at the input channel outlet 68 reaches the diastolic pressure. It is also contemplated that in some embodiments, the valve 67a could close, and the valve 67b could open before the fluid pressure at the input channel outlet 68 reaches the diastolic pressure. In yet other embodiments, the valve 67*b* and the valve 67*a* could be timed to, respectively, open and close, thereby restarting the cardiac cycle. In embodiments where the valves 67*a*, 67*b* open and/or close based on time, at least some of the control elements can be operated to make fluid pressure match their desired values.

From the input channel outlet 68, the fluid perfuses through the target member 30, and exits therefrom through the output channel inlet 78. The fluid flows in the output channel 70, and passes through the filter 77. The filter 77 captures any debris and/or clots that could be present in the fluid.

It will be appreciated that the above described operation can be adapted to achieve fluid flow profiles which differ from that illustrated in FIG. 2A. For example, the fluid flow profile may include those induced by "abnormal" heart rhythms (arrhythmia), such as but not limited tachycardia, atrial fibrillation, atrial flutter, bradycardia, ventricular fibrillation, premature contractions. In this manner, a simulation of many different health states can be achieved. In some embodiments, to achieve some fluid flow profiles, the operation of the perfusion system 24 could change. For instance, in some embodiments, the valves 67*a*, 67*b* could open at the same time, such that fluid pressure at the input channel outlet 68 could be a sum of the pressures in the branches 120*a*, 120*b*.

Figure 11:
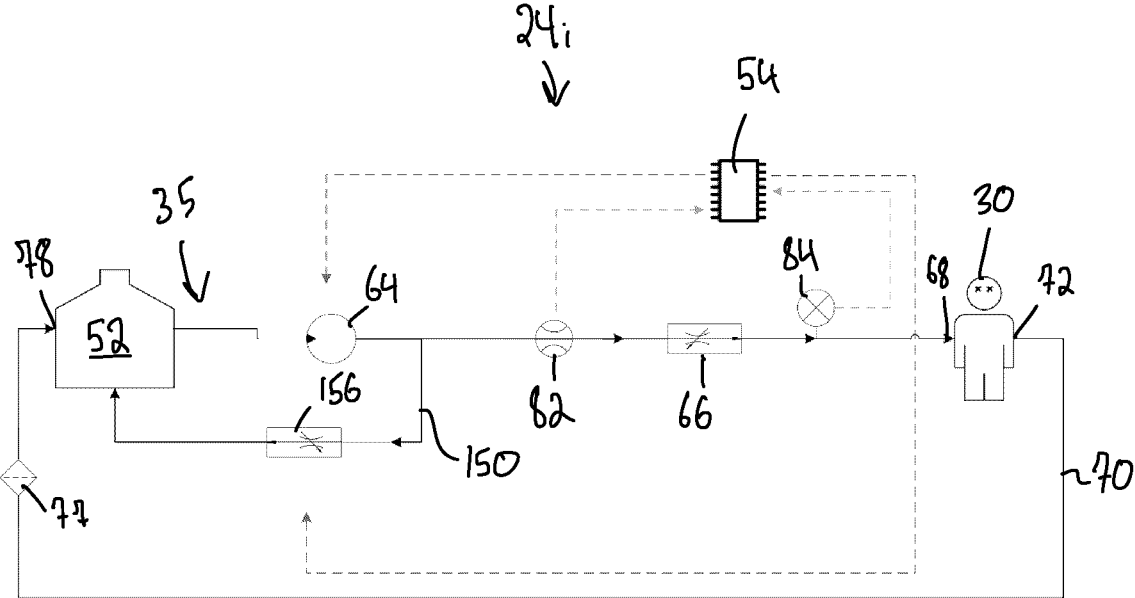
FIG. 11 is a schematic diagram of a perfusion system connected to a test member, according to certain embodiments of the present technology.

An alternative embodiment of the perfusion system 24, namely perfusion system 24*i*, will now be briefly described in reference to FIG. 11. Features of the perfusion system 24*i* that are similar to those of the perfusion systems 24*a*, 24*b*, 24*c*, 24*d*, 24*e*, 24*f*, 24*g*, 24*h* described above have been labeled with the same reference numerals and will not be described in detail again.

The perfusion system 24*i*, which is fluidly connected to the target member 30, includes the reservoir 52, the input channel 60, the pump 64, the sensors 82, 84, and the input valve 66, and the output channel 70. Thus, in the present embodiment, the output valve 76, and the output sensors 86, 88 are omitted.

In this embodiment, the perfusion system 24*i* has a feedback line 150 that is fluidly connected to the input channel 60 and to the reservoir 52. A flow control valve 156 is operatively connected to the feedback line 156 and is communicatively connected to the processor 54. The flow control valve 156 is similar to the input valve 66. Additionally, in this embodiment, the sensor 82 is disposed downstream from the fluid line 150 and upstream from the input valve 66.

Briefly, in this embodiment, the input valve 66 can control the pressure profile of the fluid perfused in the target member 30 using the processor 54 using a setpoint pressure or flow rate and feedback measurements from the pressure and flow sensors 82, 84. In some embodiments, the processor 54 could use a matrix of multiple setpoints. The perfusion system 24*i* can simulate pulsatility by alternating the input valve 66 between a fully open (systolic pressure) and a fully closed (diastolic pressure) configuration. Partially open and/or closed configurations are also possible. The specific valve configuration, in terms of its open/closed state, can be varied to obtain the desired systolic and diastolic pressures. The input valve 66 can be adjusted dynamically to perfuse the target member 30 with the predetermined fluid flow profile. In some instances, the input valve 133 can be adjusted based on the readings of the flow and pressure sensors 82, 84.

Being that the input and output valves 66, 76 are proportional valves, the flow control valves 66, 76 are configured to be adjusted to a generally open configuration which corresponds to a systolic configuration. The size of the opening of the input and output valves 66, 76 when in the systolic configuration depends on the desired systolic pressure. The input valves 66, 76 are also configured to be adjusted to a generally closed configuration which corresponds to the diastolic configuration. The size of the opening of the input valves 66, 76 when in the diastolic configuration depends on the desired diastolic pressure.

Rapid opening of the input and output valves 66, 76 to their systolic configuration creates a pressure and flow rate spike of the fluid perfused to the test member 30, as the fluid accumulates before the input and output valves 66, 76 are adjusted to their systolic configuration. Rapid closing of the input and output valves 66, 76 to their diastolic configuration results in a decrease in pressure and flow rate of the fluid perfused to the test member 30. The rate of opening and closing the input and output valves 66, 76 can be controlled dynamically by the processor 54, as desired.

The outlet valve 76 can be controlled dynamically to model systemic resistance and compliance of rest of the body, when the perfusion system 24 is connected to only the test member 30, which is part of the body.

The perfusion system 24 can thus be used to model physiological blood flow inside a synthetic organ. This can be used to test medical devices and measure pressure gradients. Desired physiological pressure profiles can be simulated. This can offer a personalized approach to simulating physiological conditions for a given patient, or group of patients, for example to practice surgery, treatment, implantation etc.

Figure 12:
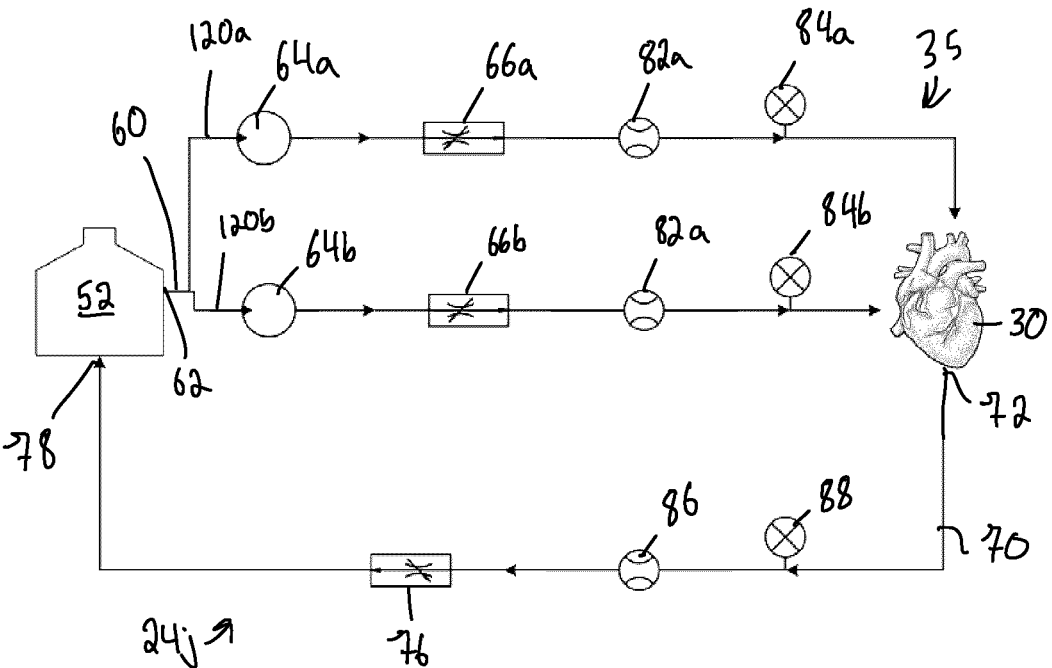
FIG. 12 is a schematic diagram of a perfusion system connected to a test member, according to certain embodiments of the present technology.

Referring to FIG. 12, an alternative embodiment of the perfusion system 24, namely perfusion system 24*j*, will now be described. Features of the perfusion system 240 that are similar to those of the perfusion systems 24*a*, 24*b*, 24*c*, 24*d*, 24*e*, 24*f*, 24*g*, 24*h*, 24*i* have been labelled with the same reference numerals and will not be described in detail herewith. The perfusion system 24*j* includes the reservoir 52, the input channel 60, the output channel 70, control elements and the processor 54.

The perfusion system 24*j* is similar to the perfusion system 24*i*, in that the input channel 60 has two branches 120*a*, 120*b*. However, in this embodiment, each of the branches 120*a*, 120*b* are fluidly connectable to the target member 30 (i.e., do not merge back together). Also, in the perfusion system 24*j* the feedback lines are omitted.

The input channel 60 has the branch 120*a*, 120*b*. Unlike embodiment 24.

Thus, the branch 120*a* has the pump 64*a*, the input valve 66*a* and the sensors 82*a*, 84*a*, and the branch 120*b* has the pump 64*b*, the input valve 66*b* and the sensors 82*b*, 84*b*.

The perfusion system 24*j* having the two input branches 120*a*, 120*b* enables the perfusion system 23*j* to perfuse the test member 30 with two points of entries.

Referring to FIG. 14, a method 300 for simulating fluid flow having a target fluid flow profile in a fluid circuit when a perfusion system, such as the perfusion system 24, is connected to a test member, such as the test member 30, will now be described. The method 300 is executed by a processor, such as the processor 54 communicatively connected to the perfusion system. The method 300 or one or more steps thereof may be embodied in computer-executable instructions that are stored in a computer-readable medium, such as a non-transitory mass storage device, loaded into memory and executed by a CPU. The method 300 is exemplary, and it should be understood that some steps or portions of steps in the flow diagram may be omitted and/or changed in order.

The method begins at step 302, where input of the target fluid flow is obtained by the processor 54. The target fluid flow profile includes a target pulsatile flow component and optionally a target systemic resistance component.

At step 304, a first valve, such as the input valve 66, in an input channel of the perfusion system 24 is controlled to generate the target pulsatile flow component in the input channel based on a predetermined first valve parameter.

At step 306, a second valve, such as the output valve 76, in an output channel of the perfusion system is controlled to generate the target systemic resistance component based on a predetermined second valve parameter.

In some embodiments, at steps 304 and 306, at least one of the first valve parameter and the second valve parameter is a voltage to be applied to the at least one of the first valve and the second valve. The first and second valves may comprise solenoid valves, such as a solenoid proportional valve.

In some embodiments, the target fluid flow profile simulates blood flow during a systole phase and a diastole phase of a heart cycle, and the processor 54 is configured to cause the input valve 66 to substantially open to simulate a start of the systole phase, and substantially close to simulate a peak arterial pressure during the systole phase and before the diastole phase. In certain embodiments, an extent of the opening of the input valve in a fully open configuration is determined to modulate a maximum desired fluid pressure in the fluid circuit.

In some embodiments, an interval between the input valve 66 being substantially open and being substantially closed is determined according to a desired relative duration of the systole phase and the diastole phase in the target fluid flow profile.

In some embodiments, an interval of the systole phase comprises a product of a (ratio of the desired relative duration of the systole and diastole phases) with (60/heart rate). In some embodiments, an interval of the diastole phase comprises a product of (1–(ratio of the desired relative duration of the systole and diastole phases)) with (60/heart rate).

In some embodiments, the processor 54 causes the output valve 76 to substantially close at the peak arterial pressure during the systole phase and before the diastole phase.

In some embodiments, the method 300 further includes the processor 54 determining the predetermined second valve parameter by modulating the output valve 76 between being open and closed, obtaining measured values of the fluid flow while the output valve 76 is modulated between being open and closed; and determining a given second valve parameter as being the predetermined second valve parameter when the target system resistance component is achieved.

In some embodiments, the method 300 further includes the processor 54 determining the predetermined first valve parameter by modulating the input valve 66 between being open and closed: obtaining measured values of the fluid flow while the input valve 66 is modulated between being open and closed; and determining a given first valve parameter as being the predetermined first valve parameter when the target pulsatile flow component is achieved.

In some embodiments, the method 300 further includes the processer 54 causing to display on the display 56 various parameters related to one or both of the target fluid flow profile (including at least one of: the target pulsatile flow component, and the target systemic resistance component), and at least one fluid flow parameter induced in the fluid circuit and measured by a sensor. In some embodiments, the display 56 displays the target fluid flow profile graph (such as FIG. 2A), and/or a measured fluid flow profile graph (such as FIG. 2B).

In some embodiments, the parameters of the target fluid flow profile and/or the measured fluid flow profile include, without limitation, one or more of: number of heart cycles, a heart cycle frequency, a systole to diastole ratio of each heart cycle, pulse intensity, flow rate average over each heart beat cycle, volume input of the model, a volume output of the model, input and/or output average pressures and pressure continuous curves, input and/or output average temperatures, and/or diastolic and systolic pressures in each heartbeat cycles.

The processor may be configured to cause the display of any one of the parameters of the target fluid flow profile. In some instances, the heart frequency can be shown in beats per minutes. The heart frequency can be calculated by the processor 54 by calculating a time interval between each start of systole. It is to be noted that in some instances, the heart frequency can be set by a user, or can be automatically controlled depending on a given scenario. Furthermore, the heart frequency can be adjusted by an operator via the display 56 as the perfusion is happening, i.e. in real time.

In some embodiments, the display 56 could display the systole to diastole ratio. This ratio can be calculated by the processor 54 by calculating the interval between the input valve 66 opening and the output valve opening 76. It is to be noted that in some embodiments, the systole to diastole ratio can be adjusted by an operator via the display 56 as the perfusion is happening, i.e. in real time.

In some embodiments, the display 56 could display a pulse intensity, which can be a representation of the voltage being sent to the valves (100% pulse intensity would imply maximum voltage, and thus the valve being fully open during easy systole, whereas 80% pulse intensity would imply 80% of maximum voltage, and thus the valve being 80% open during systole). The pulse intensity can be adjusted by an operator via the display 56 as the perfusion is happening, i.e. in real time, if the operator thinks pressure is too high, or low, for their needs.

In some embodiments, the display 56 could display a flow rate average over each heart beat cycle. Furthermore, the display 56 could also display a volume input of the model, a volume output of the model, input and/or output average pressures and pressure continuous curves, input and/or output average temperatures, and/or diastolic and systolic pressures in each heartbeat cycles.

The display 56 could also display different predetermined target fluid flow profiles (also referred to as "modes"). Some of modes include: pulsatile mode, continuous (flow controlled) mode, continuous (pressure controlled) mode, cleaning mode, simulation start mode, student mode (in which only sensed values are displayed), or a specific scenario mode (such as arrythmia or tachycardia). It is to be noted that a given mode can be selected by an operator via the display 56. When the processor obtains an input of a selection of a given one of the plurality of target flow profiles, the processor then modulates one or more of the input valve, output valve and the pump according to predetermined instructions for opening and closing the valves according to predetermined timings in order to induce the given target fluid profile in the fluid circuit.

In certain embodiments, a given mode that has been selected can be further modulated by the operator. Thus, for example, the operator could initially select a simulation start mode, then choose a pulsatile mode, and then select a clean mode. As an example, the operator could select a given mode, then adjust a value of one or more of the parameters such as heart frequency, systolic-to-diastole ratio, and pulse intensity.

Referring to FIG. 15, another embodiment of the method 300, namely method 301, will now be described.

The method 301 begins at step 310, where the processor 54 obtains input of the target fluid flow profile having a target pulsatile flow component and optionally a target systemic resistance component.

Then, at step 312, the processor 54 controls the input valve 66 based on a preliminary first valve parameter, and obtains input from a sensor of a measured fluid flow parameter in the input channel 60.

Then, at step 314, the processor 54 adjusts the preliminary first valve parameter until the measured fluid flow parameter corresponds to the target pulsatile flow component.

Then, at step 316, the processor 54 controls the output valve 76 based on a second preliminary second valve parameter, and obtains input from a sensor of a measured fluid flow parameter.

Then, at step 318, the processor 54 adjusts the second preliminary second valve parameter until the measured fluid flow parameter corresponds to the target systemic resistance component.

From another aspect, there is provided a method, executed by a processor, such as the processor 54, for simulating a target fluid flow profile in a fluid circuit when a perfusion system, such as the perfusion system 24, is connected a test member, such as the test member 30. The method comprises causing an input valve on an input channel of the perfusion system and which input valve is upstream of the test member to have a substantially open configuration to simulate a start of a systole phase of the target fluid flow profile. The method may comprise causing the input valve to have a substantially closed configuration to simulate a peak arterial pressure of the systole phase.

Figure 16:
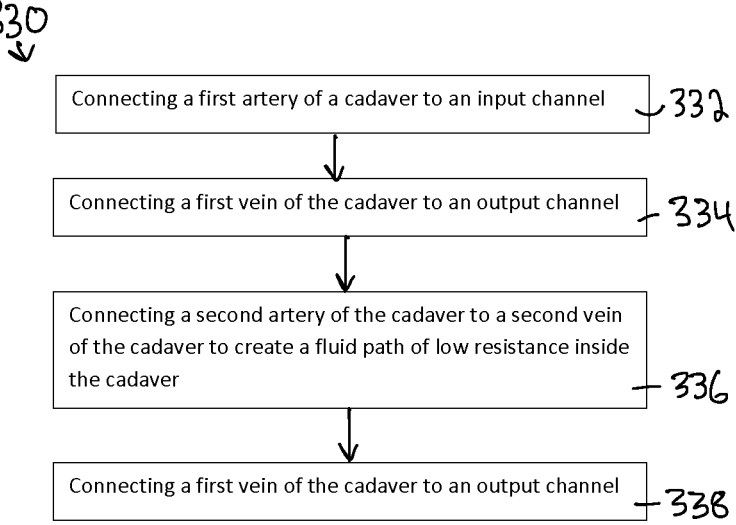
FIG. 16 is a flowchart of a method for perfusing a fluid in a target member using for example the perfusion system according to the present technology.

Referring to FIG. 16, a method 330 for perfusing fluid in a test member 30, where the test member 30 is a cadaver 30, with a perfusion system such as the perfusion system 24, will now be described. The method 330 is exemplary, and it should be understood that some steps or portions of steps in the flow diagram may be omitted and/or changed in order. The method 330 may be considered as a set-up phase, to connect the perfusion system 24 to the cadaver 30. The method 350 may be performed by a clinician, a technician or the like.

The method begins at step 332, where the input channel 60 of the perfusion system 24 is connected to an artery of the cadaver 30.

At step 334, the output channel 70 of the perfusion system 24 is connected to a vein of the cadaver 30.

At step 336, another artery of the cadaver 30 is connected to another vein of the cadaver 30 to create a fluid path of low resistance inside the cadaver 30 and flowing between artery-vein. The order of artery—vein connections is not important and can differ from above.

Then, at step 338, perfusion of the cadaver 30 through the input channel 60 with a fluid is started.

In some embodiments, the method 330 further includes increasing a pressure and flow rate of the fluid during perfusion until clots are flushed out from the cadaver 30.

In some embodiments, the method 330 includes detecting pressure and flow rate of the fluid while increasing pressure and flow rate and/or applying the fluidic shock valves.

In some embodiments, the method 330 includes sending an alarm in response to sensors being triggered upon measured fluid parameters exceeding predetermined parameters.

Figure 17:
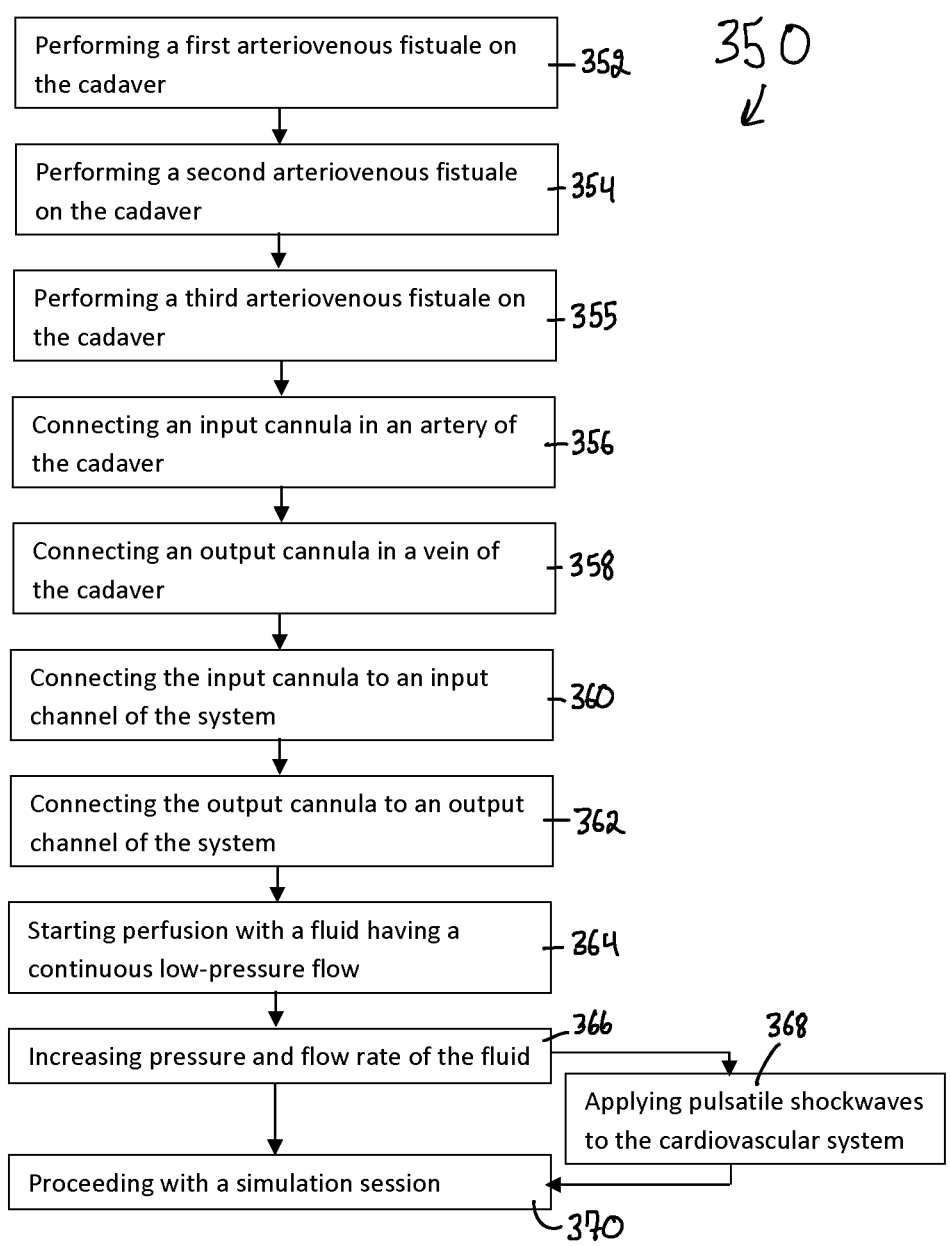
FIG. 17 is a flowchart of a method for perfusing a fluid in a target member using for example the perfusion system according to the present technology.

Referring to FIG. 17, a method 350 of perfusing a fluid in a test member, such as the test member 30 where the test member 30 is a cadaver, will now be described. The cadaver 30 may have been prepared using standard embalming methods. The method 350 may be considered as a set-up phase, to connect the perfusion system 24 to the cadaver 30. The method 350 may be performed by a clinician, a technician or the like.

The method 350 begins at step 352, where an arteriovenous fistulae is performed on the cadaver 30. The arteriovenous fistulae can be performed in the neck of the cadaver 30.

Then, at step 354, another arteriovenous fistulae is performed on the cadaver 30. This arteriovenous fistulae can be performed in one of the two femoral accesses.

Then, at step 355, another arteriovenous fistulae is performed on the cadaver 30. This arteriovenous fistulae can be performed in the other of the two femoral accesses.

Performing steps 352, 354, 355 closes the arteriovenous circuit of the cadaver 30 without requiring capillary flow to complete the arteriovenous circuit. It is contemplated that in some embodiments, the arteriovenous fistulae could be performed elsewhere on the cadaver 30. For instance, in some embodiments where a liver of the cadaver is to be perfused, one of the arteriovenous fistulae could be performed between the hepatic artery and the inferior vena cava. In yet other embodiments where an arm of the cadaver is to be perfused, one of the arteriovenous fistulae could be performed between a brachial artery and a cephalic vein of the cadaver 30.

At step 356, an input cannula is connected to an artery of the cadaver 30.

At step 358, an output cannula is connected to a vein of the cadaver 30.

It is contemplated that in some embodiments, the input cannula could be connected to a vein, and the output cannula could be connected to an artery.

At step 360, the input channel outlet 68 is connected to the input cannula.

At step 362, the output channel inlet 72 is connected to the output cannula.

At step 364, perfusion with a fluid having a continuous low-pressure flow is started to avoid rupturing the blood vessels of the cadaver 30.

Then, at step 366, flow and pressure of the fluid are slowly increased. In instances where pressure spikes are detected by the pressure sensor 82, fluid flow and pressure could be reduced. The flow and pressure of the fluid are increased slowly to avoid rupturing the blood vessels of the cadaver 30.

In some instances, fluid flow can stop due to clots and/or debris present in the cardiovascular circuit of the cadaver 30. In such instances, a step 368 could arise, where the cardiovascular circuit of the cadaver 30 is perfused with pulsatile shockwaves of generally low magnitude compared to the perfusion fluid flow and fluid pressure to dislodge the clots and/or debris. In some embodiments, the frequency of the pulsatile shockwaves could be between about 2 and about 20 hertz. In some embodiments, the pulsatile shockwaves may have a pressure of about 20 mm Hg and about 150 mm Hg. In some embodiments, the pressure of the pulsatile shockwaves may be sequentially increased. The pulsatile shockwaves may have a sine-wave like profile with an amplitude less than a mean pressure. For example, for a mean pressure of 60 mm Hg, the amplitude of the shock wave profile may vary between about 45 and 75 mm Hg.

Then, at step 3720, once desired fluid pressure and flow rate have been reached, a fluid flow simulation session can begin.

Figure 18:
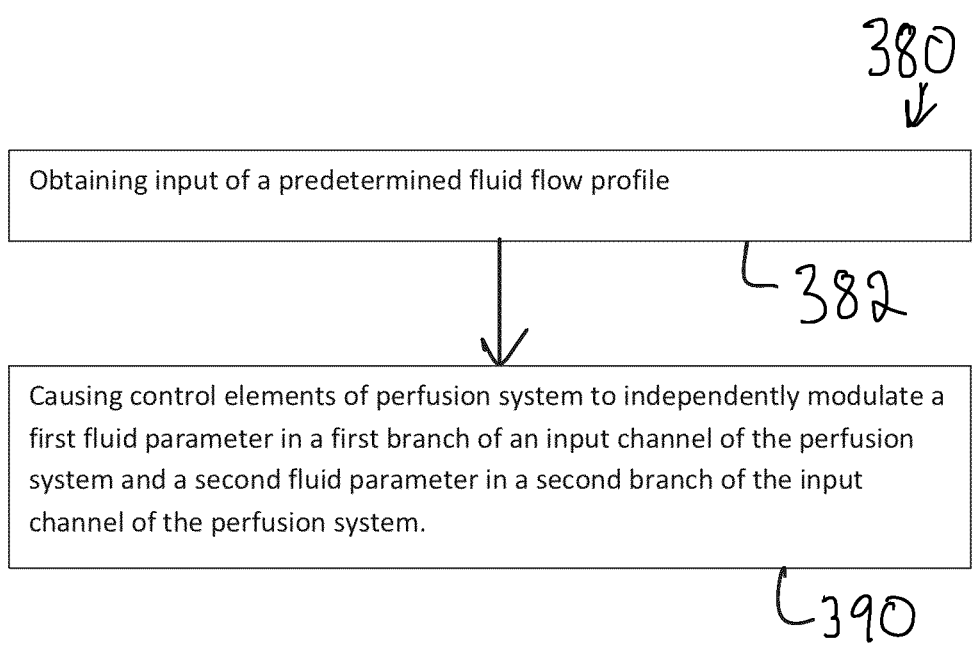
FIG. 18 is a flowchart of a method for perfusing a fluid in a target member using for example the perfusion system according to the present technology.

A method for perfusing the cardiovascular circuit 62 with a predetermined fluid flow profile will now be described with reference to FIG. 18. The method 380 can be performed by the processor 54 of a computer system, such as the processor 205 of the computing environment 200. The processor 54 may include machine readable instructions enabling it to perform the described method steps. As mentioned above, the processor 54 is connected to, and configured to modulate, the pumps 66, the valves 66, 76, 67, 136, 146, and the sensors 82, 84, 86, 88.

A method 380 begins at step 382 with the processor 54 obtaining input of a predetermined fluid flow profile. The processor 54 may retrieve the predetermined fluid flow profile from a memory, such as the memory 204, or the processor 54 may obtain the predetermined fluid flow profile as an input by a user of the prefusion system 24. The predetermined fluid flow profile is the fluid flow profile that the fluid being perfused in the target member 30 will follow. The predetermined fluid flow profile could be a physiological blood pressure profile, a pathological pressure profile or a problematic arterial pressure profile. The predetermined fluid flow profile may contain instructions to the processor 54 regarding a desired fluid pressure profile in branch 120a, a desired fluid pressure profile in branch 120b and a desired fluid pressure profile at the input channel outlet 68, in order to obtain the predetermined fluid flow profile of the fluid in the target member 30. In the present embodiment, the branch 120a is a diastolic branch 120a, and the branch 120b is a systolic branch 120b.

At step 390, the processor 54 is configured to cause at least some of the control elements to independently modulate a fluid parameter in the diastolic branch 120a and modulate a fluid parameter in the systolic branch 120b so as to obtain the predetermined fluid flow at the input channel outlet 68, and thus perfuse the target member 30 according to the predetermined fluid flow profile.

In some embodiments, step 390 includes the processor 54 causing operation of the pumps 64a, 64b to cause fluid flow from the reservoir 52 to the diastolic and systolic branches 120a, 120b.

In some embodiments, step 390 includes the processor 54 obtaining a detected pressure in the diastolic branch 120a. If the detected pressure does not correspond to the desired pressure in the diastolic branch 120a, then step 390 includes the processor 54 causing at least some of the control elements, such as the input valve 66 to modulate the detected pressure until the detected pressure corresponds to the desired pressure. In some embodiments, the processor 54 may cause the control element such as the valve 136 on the feedback line 130a to modulate the detected pressure until the detected pressure corresponds to the desired pressure.

In some embodiments, step 390 includes the processor 54 obtaining a detected pressure in the systolic branch 120b. If the detected pressure does not correspond to the desired pressure in the systolic branch 120b, then step 390 includes the processor 54 causing at least some of the control elements, such as the input valve 66b to modulate the detected pressure until the detected pressure corresponds to the desired pressure. In some embodiments, the processor 54 may cause the control element such as the valve 136b on the feedback line 130b to modulate the detected pressure until the detected pressure corresponds to the desired pressure.

In some embodiments, step 390 also includes the processor 54 obtaining a detected pressure at the input channel outlet 68. If the detected pressure does not correspond to the desired pressure at the input channel outlet 68, then step 390 includes the processor 54 causing at least some of the control elements, such as the valves 66a, 66b to modulate the detected pressure until the detected pressure corresponds to the desired pressure. In some embodiments, the processor 54 may cause the control element such as the valve 146 on the feedback line 140 to modulate the detected pressure until the detected pressure corresponds to the desired pressure.

In some embodiments, the detected pressures are modulated in real-time, such that if the predetermined pressure profile is updated during perfusion, which results in updated desired pressures, the processor 54 causes at least some of the control elements to modulate the detected pressures to correspond to the updated desired pressures.

In some embodiments, the step 390 includes the processor 54 causing the display 56 to display any one of the detected pressure in the branch 120a, the detected pressure in the branch 120b, the detected pressure at the input channel outlet 114, the desired pressure in the branch 120a, the desired pressure in the branch 120b, the desired pressure at the input channel outlet 68.

In some embodiments, if the detected pressure corresponds to the desired pressure, then step 390 includes the processor 54 causing the control elements to maintain pressure in the diastolic branch generally constant, and causing the control elements such as the valves 66a, 66b to modulate pressure in the systolic branch between minimum and maximum values. In some embodiments, the maximum pressure in the systolic branch could be 120 mmHg, and the minimum pressure could be 60 mmHg. In some embodiments, the pressure in the diastolic branch could be 80 mmHg.

In some embodiments, where the predetermined fluid flow profile is a physiological blood pressure profile such as the profile illustrated in FIG. 2A, step 390 includes the processor 54 causing the valve 67a to block fluid flow in the diastolic branch 120a, causing the valve 67b to block fluid flow in the systolic branch 120b, modulating control elements in the diastolic branch 120a to obtain a diastolic pressure in the diastolic branch 120a, modulating control elements in the systolic branch 120b to obtain a diastolic pressure in the diastolic branch 120b, opening the valve 67b thereby allowing fluid from the systolic branch 120b towards the input channel outlet 68, causing control elements to modulate the systolic pressure so as to reduce systolic pressure, simultaneously opening the valve 67a and closing the valve 67b, thereby allowing fluid flow from the diastolic branch 120a towards the input channel outlet 68, and blocking fluid from the systolic branch 120b.

Modifications and improvements to the above-described embodiments of the present invention may become apparent to those skilled in the art. The foregoing description is intended to be exemplary rather than limiting. The scope of the present invention is therefore intended to be limited solely by the appended claims.

What is claimed is:

1. A method for perfusing a fluid in a cadaver or a portion of the cadaver using a system for simulating cardiovascular fluid flow having a target fluid flow profile, the method comprising:

connecting a first artery of the cadaver or the portion of the cadaver to an input channel of the system;

connecting a first vein of the cadaver or the portion of the cadaver to an output channel of the system;

connecting a second artery of the cadaver or the portion of the cadaver to a second vein of the cadaver to create a fluid path of low resistance inside the cadaver or the portion of the cadaver; and starting perfusion of the cadaver or the portion of the cadaver through the input channel with a fluid.

2. The method of claim 1, further comprising increasing a pressure and flow rate of the fluid during perfusion until clots are flushed out from the cadaver or the portion of the cadaver.

3. The method of claim 1, further comprising applying fluidic shock waves to the fluid during perfusion.

4. The method of claim 1, further comprising connecting one or more of (i) the artery to the input channel, and (ii) the vein to the output channel using a cannula.

5. The method of claim 1, wherein:

the target fluid flow profile comprises a target pulsatile flow component and a target systemic resistance component;

the system further comprises:

a first valve positioned within the input channel operable between an open configuration and a closed configuration for modulating fluid flow in the input channel; and a second valve positioned within the output channel operable between an open configuration and a closed configuration for modulating fluid flow in the output channel;

the method further comprising:

controlling the first valve to generate the target pulsatile flow component in the input channel; and controlling the second valve to generate the target systemic resistance component.

6. The method of claim 1, wherein:

the system further comprises:

a first valve positioned the input channel, the input channel configured to supply fluid to the first artery; and a processor communicatively coupled to the first valve;

the method further comprises:

obtaining input, by the processor, of the target fluid flow profile, the target fluid flow profile comprising a target pulsatile flow component; and controlling the first valve to generate the target pulsatile flow component in the input channel based on a predetermined first valve parameter.

7. The method of claim 6, wherein the first valve is a proportional solenoid valve, and the first valve parameter is a voltage to be applied to the first valve.

8. The method of claim 6, wherein:

the system further comprises:

a second valve positioned in the output channel, the output channel configured to receive fluid from the first vein;

the processor communicatively coupled to the second valve; and the target profile further comprises a target systemic resistance component;

the method further comprises:

controlling the second valve to generate the target systemic resistance component based on a predetermined second valve parameter.

9. The method of claim 8, wherein the second valve is a proportional solenoid valve, and the second valve parameter is a voltage applied to the second valve.

10. The method of claim 7, further comprising:

causing, by the processor, the proportional solenoid valve to have a substantially open configuration to simulate a start of systole phase of the target fluid flow profile, and to have a substantially closed configuration to simulate a peak arterial pressure of the systole phase.

11. The method of claim 6, wherein the target fluid flow profile simulates blood flow during a systole phase and a diastole phase of a heart cycle, the processor configured to cause the first valve to:

substantially open to simulate a start of the systole phase, and substantially close to simulate a peak arterial pressure during the systole phase and before the diastole phase.

12. The method of claim 11, wherein an interval between the first valve being substantially open and being substantially closed is determined according to a desired relative duration of the systole phase and the diastole phase in the target pulsatile flow.

13. The method of claim 12, wherein an interval of the systole phase comprises (ratio of the desired relative duration of the systole and diastole phases)*(60/heart rate) and an interval of the diastole phase comprises (1−(ratio of the desired relative duration of the systole and diastole phases))*(60/heart rate).

14. The method of claim 11, wherein:

the system further comprises:

a second valve in the output channel of the perfusion system;

the processor communicatively coupled to the second valve; and the target profile further comprises a target systemic resistance component;

the method further comprises:

controlling the second valve to generate the target systemic resistance component based on a predetermined second valve parameter.

15. The method of claim 14, further comprising the processor causing the second valve to substantially close at the peak arterial pressure during the systole phase and before the diastole phase.

16. The method of claim 14, further comprising the processor determining at least one of:

the predetermined second valve parameter by modulating the second valve between being open and closed; obtaining measured values of the fluid flow while the second valve is modulated between being open and closed; and determining a given second valve parameter as being the predetermined second valve parameter when the target system resistance component is achieved; and the predetermined first valve parameter by modulating the first valve between being open and closed; obtaining measured values of the fluid flow while the first valve is modulated between being open and closed; and determining a given first valve parameter as being the predetermined first valve parameter when the target pulsatile flow component is achieved.

17. The method of claim 1, wherein:

the system further comprises:

a display; and a processor communicatively coupled to the display, the input channel, and the output channel; and the method further comprises:

detecting a fluid parameter in one or both of the input channel and the output channel, and causing, by the processor, to display, on the display, the fluid parameter.

18. A method for simulating a target fluid flow profile in test member when a perfusion system is connected to the test member to create a fluid circuit therewith, the method being executed by a processor communicatively coupled to:

a first valve in an input channel of the perfusion system, the input channel configured to supply fluid to the test member when connected thereto, and a second valve in an output channel of the perfusion system, the output channel configured to receive fluid from the test member when connected thereto, the method comprising:

obtaining input, by the processor, of the target fluid flow profile, the target fluid flow profile comprising a target pulsatile flow component and a target systemic resistance component;

controlling, by the processor, the first valve based on a preliminary first valve parameter, and obtaining input from a sensor of a measured fluid flow parameter in the input channel;

adjusting the preliminary first valve parameter until the measured fluid flow parameter corresponds to the target pulsatile flow component;

controlling the second valve based on a second preliminary second valve parameter, and obtaining input from a sensor of a measured fluid flow parameter; and adjusting the second preliminary second valve parameter until the measured fluid flow parameter corresponds to the target systemic resistance component.

\* \* \* \* \*